United States Patent [19]

Takaya et al.

[11] 4,394,384

[45] Jul. 19, 1983

[54] AMINOTHIAZOLE CYCLOALKENYLOXYIMINO ACETAMIDO CEPHEM DERIVATIVES

[75] Inventors: Takao Takaya, Kawanishi; Hisashi Takasugi, Kohamanishi; Masayoshi Murata, Mino; Akiteru Yoshioka, Kyoto, all of Japan

[73] Assignee: Fujisawa Pharmaceutical Co., Ltd., Osaka, Japan

[21] Appl. No.: 183,167

[22] Filed: Sep. 2, 1980

[30] Foreign Application Priority Data

Sep. 3, 1979 [GB] United Kingdom ................. 7930515
Jun. 2, 1980 [GB] United Kingdom ................. 8018006

[51] Int. Cl.$^3$ .................. A61K 31/545; C07D 501/34; C07D 501/56
[52] U.S. Cl. ...................................... 424/246; 544/22; 544/25; 544/27; 544/28; 548/194
[58] Field of Search ..................... 544/27, 28; 424/246

[56] References Cited

U.S. PATENT DOCUMENTS 3,971,778  7/1976  Cook et al. ........................... 544/27
4,196,205  4/1980  Heymes et al. ...................... 544/28
4,294,960  10/1981  Takaya et al. ....................... 544/28

FOREIGN PATENT DOCUMENTS 865632 10/1978 Belgium .

Primary Examiner—Paul M. Coughlan, Jr.
Attorney, Agent, or Firm—Oblon, Fisher, Spivak, McClelland & Maier

[57] ABSTRACT

The invention relates to new cephem compounds of high antimicrobial activity, the new cephem compounds comprising aminothiazole cycloalkenyloxyimino acetamido cephem derivatives.

11 Claims, No Drawings

AMINOTHIAZOLE CYCLOALKENYLOXYIMINO ACETAMIDO CEPHEM DERIVATIVES

The present invention relates to new cephem compounds and pharmaceutically acceptable salts thereof. More particularly, it relates to new cephem compounds and pharmaceutically acceptable salts thereof, which have antimicrobial activities and to processes for preparation thereof, to pharmaceutical composition comprising the same, and to a method of using the same therapeutically in the treatment of infectious diseases in human being and animals.

Accordingly, it is one object of the present invention to provide new cephem compounds and pharmaceutically acceptable salts thereof, which are active against a number of pathogenic microorganisms.

Another object of the present invention is to provide processes for the preparation of new cephem compounds and pharmaceutically acceptable salts thereof.

A further object of the present invention is to provide pharmaceutical composition comprising, as active ingredients, said new cephem compounds and pharmaceutically acceptable salts thereof.

Still further object of the present invention is to provide a method for the treatment of infectious diseases caused by pathogenic bacteria in human being and animals.

The object new cephem compounds are novel and can be represented by the following general formula (I).

(I)

wherein
$R^1$ is amino or a protected amino group,
$R^2$ is cyclo(lower)alkenyl,
$R^3$ is carboxy or a protected carboxy group, and
$R^4$ is hydrogen or a group of the formula:

—$CH_2$—$R^{4a}$ (wherein $R^{4a}$ is acyloxy, amino(lower)alkylthio, a protected amino(lower)alkylthio group, pyridinium which may have suitable substituent(s), or a heterocyclicthio group which may have suitable substituent(s), and
$R^5$ is hydrogen or lower alkyl,
with proviso that $R^3$ is $COO^-$ when $R^{4a}$ is pyridinium which may have suitable substituent(s).

According to the present invention, the new cephem compounds (I) can be prepared by various processes which are illustrated in the following schemes.

Process 1.

(II)   (III)

or its reactive derivative at the amino group or a salt thereof or its reactive derivative at the carboxy group or a salt thereof →

(I)

or a salt thereof

Process 2

(Ia)

or a salt thereof

Elimination of the amino protective group →

(Ib)

or a salt thereof

Process 3

(Ic)

or a salt thereof $R^{4b}$ (IX) or its reactive derivative →

(Id)

or a salt thereof

Process 4

-continued

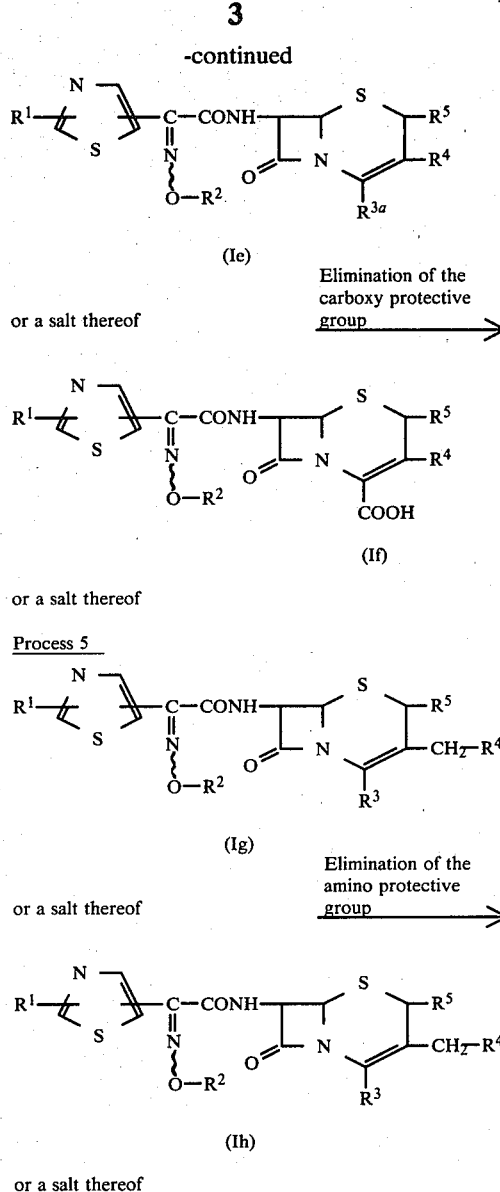

(Ie)

or a salt thereof

Elimination of the carboxy protective group ⟶

(If)

or a salt thereof

Process 5

(Ig)

or a salt thereof

Elimination of the amino protective group ⟶

(Ih)

or a salt thereof wherein
$R^1$, $R^2$, $R^3$, $R^4$, and $R^5$ are each assdefined above;
$R^{1a}$ is a protected amino group;
$R^{4b}$ is a heterocyclicthiol which may have suitable substituent(s), pyridine which may have suitable substituent(s), amino(lower)alkylthiol or a protected amino(lower)alkylthiol;
Y is a group which can be substituted by a group of the formula: —$R^{4c}$ in which $R^{4c}$ is a heterocyclicthio group which may have suitable substituent(s), pyridinium which may have suitable substituent(s), amino(lower)alkylthio or a protected amino(lower)alkylthio;
$R^{4c}$ is as defined above;
$R^{3a}$ is a protected carboxy group;
$R^{4d}$ is a heterocyclicthio group having a protected amino(lower)alkyl, a protected amino(lower)alkylthio or a protected carbamoyloxy;
$R^{4e}$ is a heterocyclicthio group having an amino(lower)alkyl, amino(lower)alkylthio or carbamoyloxy.

Among the starting compounds in the present invention, the compound (III) is novel and can be prepared by the process which are illustrated in the following schemes.

(A)

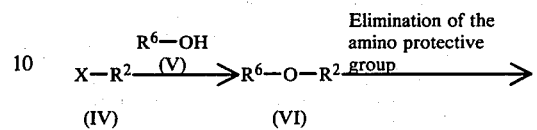

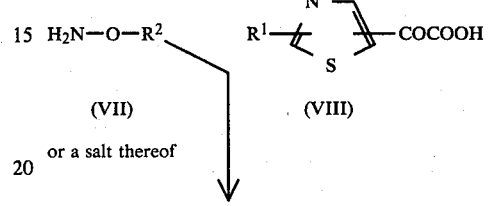

or a salt thereof

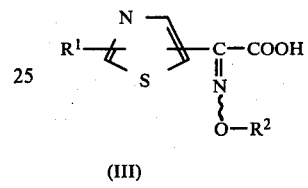

(III)

or a salt thereof (B)

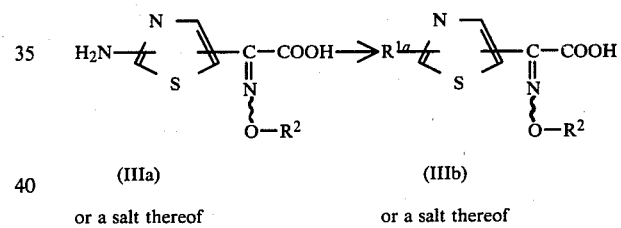

(IIIa)          (IIIb)

or a salt thereof     or a salt thereof

Moreover, the compound (II) includes the novel compounds, which can be prepared by the process illustrated in the following scheme.

(C)

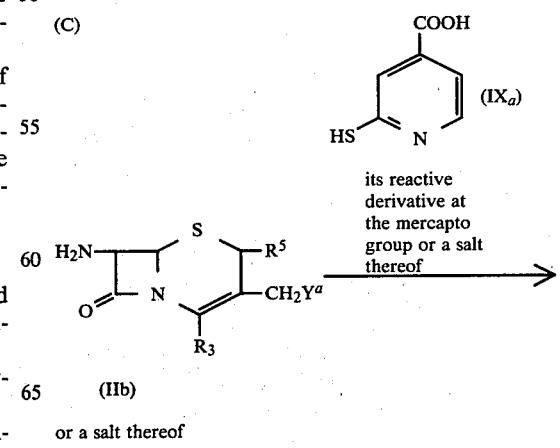

(IIb)

or a salt thereof

-continued

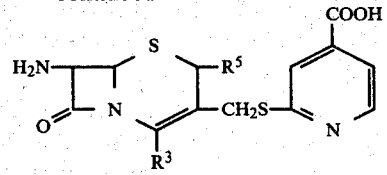

(IIa)
or a salt thereof wherein
$R^1$, $R^{1a}$, $R^2$, $R^3$ and $R^5$ are each as defined above;
$Y^a$ is a group which can be substituted by a group of the formula:

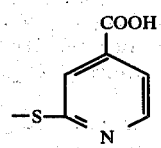

X is hydroxy or its reactive derivative, and
$R^6$ is amino having a protective group.

Regarding the object compounds (I), (Ia), (Ib), (Ic), (Id), (Ie), (If), (Ig) and (Ih) and the starting compounds (III), (IIIa), (IIIb) and (VIII), it is to be understood that they include tautomeric isomers. That is, in case that the group of the formula:

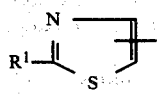

($R^1$ is as defined above) is contained in the molecules of said object and starting compounds, said group of the formula can also be alternatively represented by its tautomeric formula:

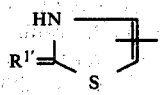

($R^{1'}$ is imino or a protected imino group). That is, the both of said groups are in the state of equilibrium each other and such tautomerism can be represented by the following equilibrium.

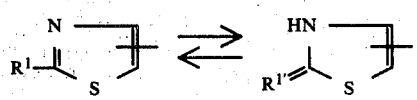

wherein $R^1$ and $R^{1'}$ are each as defined above.

These types of tautomerism between the amino-compound and the corresponding imino-compound as stated above have been well known in the literature, and it is obvious to a person skilled in the arts that both of the tautomeric isomers are easily convertible reciprocally and are included within the same category of the compound per se. Accordingly, the both of the tautomeric forms of the object compounds (I), (Ia), (Ib), (Ic), (Id), (Ie), (If), (Ig) and (Ih) and the starting compounds (III), (IIIa), (IIIb) and (VIII) are clearly included within the scope of the present invention. In the present specification and claims, the object and starting compounds including the group of such tautomeric isomers are represented by using one of the expressions therefor, that is the formula:

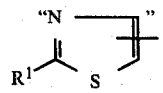

object compounds (I), (Ia), (Ib), (Ic), (Id), (Ie), (If), (Ig) and (Ih) and the starting compounds (III), (IIIa) and (IIIb), it is to be understood that said object and starting compounds include syn isomer, anti isomer and a mixture thereof. For example, with regard to the object compound (I), syn isomer means one geometrical isomer having the partial structure represented by the following formula:

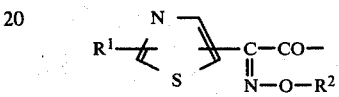

(wherein $R^1$ and $R^2$ are each as defined above) and anti isomer means the other geometrical isomer having the partial structure represented by the following formula:

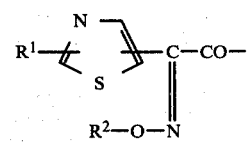

(wherein $R^1$ and $R^2$ are each as defined above).

Regarding the other object and starting compounds as mentioned above, the syn isomer and the anti isomer can also be referred to the same geometrical isomers as illustrated for the compound (I).

Suitable pharmaceutically acceptable salts of the object compounds (I) are conventional non-toxic salt and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, maleate, tartrate, methanesulfonate, benzenesulfonate, formate, toluenesulfonate, etc.), an inorganic acid salt (e.g. hydrochloride, hydrobromide, sulfate, phosphate, etc.), or a salt with an amino acid (e.g. arginine, aspartic acid, glutamic acid, etc.), and the like.

In the above and subsequent descriptions of the present specification, suitable examples and illustrations of the various definitions which the present invention include within the scope thereof are explained in details as follows.

The term "lower" is intended to mean 1 to 6 carbon atoms, unless otherwise indicated.

Suitable protected amino and protected amino moiety in the term "protected amino(lower)alkylthio", "protected amino(lower)alkylthiol" and "heterocyclicthio group having a protected amino(lower)alkyl" may include an acylamino or an amino group substituted by a conventional protecting group such as ar(lower)alkyl which may have at least one suitable substituent(s), (e.g. benzyl, trityl, etc.) or the like.

Suitable acyl moiety in the terms "acylamino" and "acyloxy" for $R^{4a}$ may include carbamoyl, aliphatic acyl group and acyl group containing an aromatic or heterocyclic ring. And, suitable examples of the said acyl may be lower alkanoyl (e.g. formyl, acetyl, propionyl, butyryl, isobutyryl, valeryl, isovaleryl, oxalyl, succinyl, pivaloyl, etc.); lower alkoxycarbonyl (e.g. methoxycarbonyl, ethoxycarbonyl, propoxycarbonyl, 1-cyclopropylethoxycarbonyl, isopropoxycarbonyl, butoxycarbonyl, tertiarybutoxycarbonyl, pentyloxycarbonyl, hexyloxycarbonyl, etc.);

lower alkanesulfonyl (e.g. mesyl, ethanesulfonyl, propanesulfonyl, isopropanesulfonyl, butanesulfonyl, etc.);

arenesulfonyl (e.g. benzenesulfonyl, tosyl, etc.); aroyl (e.g. benzoyl, toluoyl, xyloyl, naphthoyl, phthaloyl, indancarbonyl, etc.);

ar(lower)alkanoyl (e.g. phenylacetyl, phenylpropionyl, etc.);

ar(lower)alkoxycarbonyl (e.g. benzyloxycarbonyl, phenethyloxycarbonyl, etc.), and the like.

The acyl moiety as stated above may have at least one suitable substituent(s) such as halogen (chlorine, bromine, fluorine and iodine) or the like.

Preferable examples of acylamino and acyloxy groups may include lower alkanoylamino, halogen substituted lower alkanoylamino, lower alkoxycarbonylamino, lower alkanoyloxy and carbamoyloxy respectively.

Suitable cyclo(lower)alkenyl for $R^2$ may include cyclopropenyl, cyclobutenyl, cyclopentenyl, cyclohexenyl and the like.

Suitable protected carboxy for $R^3$ may include an esterified carboxy and the like, and suitable examples of the ester moiety in said esterified carboxy may be the ones such as lower alkyl ester (e.g. methyl ester, ethyl ester, propyl ester, isopropyl ester, butyl ester, isobutyl ester, pentyl ester, hexyl ester, 1-cyclopropylethyl ester, etc.) which may have at least one suitable substituent(s), for example, lower alkanoyloxy(lower)alkyl ester (e.g. acetoxymethyl ester, propionyloxymethyl ester, butyryloxymethyl ester, valeryloxymethyl ester, pivaloyloxymethyl ester, 2-acetoxyethyl ester, 2-propionyloxyethyl ester, hexanoyloxymethyl ester, etc.), lower alkanesulfonyl(lower)alkyl ester (e.g. 2-mesylethyl ester, etc.) or mono(or di or tri)-halo(lower)alkyl ester (e.g. 2-iodoethyl ester, 2,2,2-trichloroethyl ester, etc.); lower alkenyl ester (e.g. vinyl ester, allyl ester, etc.); lower alkynyl ester (e.g. ethynyl ester, propynyl ester, etc.);

ar(lower)alkyl ester which may have at least one suitable substituent(s) (e.g. benzyl ester, 4-methoxybenzyl ester, 4-nitrobenzyl ester, phenethyl ester, trityl ester, diphenylmethyl ester;

bis(methoxyphenyl)methyl ester, 3,4-dimethoxybenzyl ester, 4-hydroxy-3,5-ditertiarybutylbenzyl ester, etc.);

aryl ester which may have at least one suitable substituent(s) (e.g. phenyl ester, 4-chlorophenyl ester, tolyl ester, tertiarybutylphenyl ester, xylyl ester, mesityl ester, cumenyl ester, etc.), and the like.

Preferable example of the esterified carboxy as mentioned above may include lower alkoxycarbonyl (e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, tert-pentyloxycarbonyl, hexyloxycarbonyl, 1-cyclopropylethoxycarbonyl, etc.) and phenyl(lower)alkoxycarbonyl (e.g. benzyloxycarbonyl, diphenylmethoxycarbonyl, etc.).

The heterocyclic moiety in the terms "heterocyclicthio group which may have suitable substituent(s)", "heterocyclicthio group having a protected amino(lower)alkyl", "heterocyclicthio group having an amino(lower)alkyl", and "heterocyclicthiol which may have suitable substituent(s)" means saturated or unsaturated, monocyclic or polycyclic heterocyclic group containing at least one hetero-atom such as an oxygen, sulfur, nitrogen atom and the like. And, especially preferable heterocyclic group may be heterocyclic group such as unsaturated 3 to 8-membered heteromonocyclic group containing 1 to 4 nitrogen atom(s), for example, pyrrolyl, pyrrolinyl, imidazolyl, pyrazolyl, pyridyl and its N-oxide, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.;

saturated 3 to 8-membered heteromonocyclic group containing 1 to 4 nitrogen atom(s), for example, pyrrolidinyl, imidazolidinyl, piperidino, piperazinyl, etc.;

unsaturated condensed heterocyclic group containing 1 to 5 nitrogen atom(s), for example, indolyl, isoindolyl, indolizynyl, benzimidazolyl, quinolyl, isoquinolyl, indazolyl, benzotriazolyl, tetrazolopyridyl, tetrazolopyridazinyl, dihydrotriazolopyridazinyl, etc.;

unsaturated 3 to 8-membered heteromonocyclic group containing 1 to 2 oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc.), etc.;

saturated 3 to 8-membered heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered heteromonocyclic group containing 1 to 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered heteromonocyclic group containing 1 to 2 sulfur atom(s) and 1 to 3 nitrogen atom(s), for example, thiazolidinyl, etc.;

unsaturated 3 to 8-membered heteromonocyclic group containing 1 to 2 sulfur atom(s), for example, thienyl, dihydrodithiinyl, dihydrodithiolyl, etc.;

unsaturated condensed heterocyclic group containing 1 to 2 sulfur atom(s) and 1 to 3 nitrogen atom(s), for example, benzothiazolyl, benzothiadiazolyl, etc.; unsaturated 3 to 8-membered heteromonocyclic group containing an oxygen atom, for example, furyl, etc.;

unsaturated 3 to 8-membered heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc. and the like.

The heterocyclic moieties as mentioned above may have 1 to 3 substituent(s) such as lower alkyl (e.g.

methyl, ethyl, propyl, isopropyl, butyl, isobutyl, tert-butyl, pentyl, hexyl, etc.), lower alkenyl (e.g. vinyl, allyl, butenyl, etc.), carboxy, carboxy(lower)alkyl (e.g. carboxymethyl, carboxyethyl, carboxypropyl, etc.), hydroxy(lower)alkyl (e.g. hydroxymethyl, hydroxyethyl, hydroxypropyl, etc.), amino(lower)alkyl (e.g. aminomethyl, aminoethyl, aminopropyl, aminobutyl, etc.), protected amino(lower)alkyl (e.g. acylaminomethyl, acylaminoethyl, acylaminopropyl, acylaminobutyl therein acyl moieties are as defined above, etc.) or the like.

Preferable example of heterocyclic moieties having suitable substituent(s) may include tatrazolyl having lower alkyl (e.g. methyltetrazolyl, ethyltetrazolyl, etc.), thiadiazolyl having lower alkyl (e.g. methylthiadiazolyl, ethylthiadiazolyl, etc.), thiadiazolyl having amino(lower)alkyl (e.g. aminomethylthiadiazolyl, aminoethylthiadiazolyl, etc.), thiadiazolyl having lower alkoxycarbonylamino(lower)alkyl (e.g. t-butoxycarbonylaminomethylthiadiazolyl, etc.), tetrazolyl having lower alkenyl (e.g. vinyltetrazolyl, allyltetrazolyl, butenyltetrazolyl, etc.), tetrazolyl having carboxy(lower)alkyl (e.g. carboxymethyltetrazolyl, carboxyethyltetrazolyl, etc.), tetrazolyl having hydroxy(lower)alkyl (e.g. hydroxymethyltetrazolyl, hydroxyethyltetrazolyl, etc.), pyridyl having carboxy, tetrazolyl having amino(lower)alkyl (e.g. aminomethyltetrazolyl, aminoethyltetrazolyl, aminopropyltetrazolyl, etc.), tetrazolyl having lower alkoxycarbonylamino(lower)alkyl (e.g. t-butoxycarbonylaminomethyltetrazolyl, t-butoxycarbonylaminoethyltetrazolyl t-butoxycarbonylaminopropyltetrazolyl, etc.), and the like.

Suitable substituent(s) on pyridinium and pyridine may include 1 to 2 hydroxy(lower)alkyl as defined above, carbamoyl and the like.

Suitable lower alkyl and lower alkyl moiety in the terms "amino(lower)alkylthio", "protected amino(lower)alkylthio", "amino(lower)alkylthio" and "protected amino(lower)alkylthiol" mean straight or branched one and may include methyl, ethyl, propyl, isopropyl, butyl, isobutyl, t-butyl, pentyl, hexyl and the like.

Preferable example of amino(lower)alkylthio may include aminomethylthio, aminoethylthio, aminopropylthio and the like.

Suitable protected carbamoyl may include an acylcarbamoyl group wherein an acyl group is as defined above.

Suitable example of Y and Ya may include an acid residue (e.g. azido, aforesaid halogen, acyloxy as aforementioned, etc.) and the like.

Suitable hydroxy reactive derivative for X may include an acid residue such as halogen (e.g. chlorine, bromine, fluorine or iodine) or the like.

Suitable amino having a protective group for $R^6$ may include phthalimido, succinimido, ethoxycarbonylamino and the like, and preferably phthalimido.

The preferable examples of the object compound (I) are exemplified as follows.

Preferable example of $R^1$ is amino, lower alkanoylamino or halogen substituted lower alkanoylamino;

$R^2$ is cyclopentenyl or cyclohexenyl;

$R^3$ is carboxy or ar(lower)alkoxycarbonyl [more preferably diphenyl(lower)alkoxycarbonyl];

$R^4$ is hydrogen or a group of the formula: —CH$_2$—R$^{4a}$ [wherein preferable example of $R^{4a}$ is lower alkanoyloxy, carbamoyloxy, thiadiazolylthio which may have lower alkyl as a substituent, thiadiazolylthio having amino(lower)alkyl as a substituent, thiadiazolylthio having lower alkoxycarbonylamino(lower)alkyl as a substituent, tetrazolylthio which may have lower alkyl as a substituent, tetrazolylthio having lower alkenyl as a substituent, tetrazolylthio having carboxy(lower)alkyl as a substituent, tetrazolylthio having hydroxy(lower)alkyl as a substituent, pyridylthio having carboxy as a substituent, amino(lower)alkylthio or alkoxycarbonylamino(lower)alkylthio, tetrazolylthio having amino(lower)alkyl as a substituent, tetrazolylthio having lower alkoxycarbonylamino(lower)alkyl as a substituent, triazolylthio, tetrazolopyridazinylthio, pyridinium, pyridinium having hydroxy(lower)alkyl as a substituent, pyridinium having carbamoyl as a substituent];

$R^5$ is hydrogen or lower alkyl.

The processes for preparing the object compounds of the present invention are explained in details in the following.

Process 1

The object compound (I) or a salt thereof can be prepared by reacting the compound (II) or its reactive derivative at the amino group or a salt thereof with the compound (III) or its reactive derivative at the carboxy group or a salt thereof.

Suitable reactive derivative at the amino group of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as bis(trimethylsilyl)acetamide or the like; a derivative formed by reaction of the compound (II) with phosphorus trichloride or phosgene, and the like.

Suitable salt of the compounds (II) and (III) may include an acid addition salt such as an organic acid salt (e.g., acetate, maleate, tartrate, benzenesulfonate, toluenesulfonate, etc.) or an inorganic acid salt (e.g., hydrochloride, hydrobromide, sulfate, phosphate, etc.); a metal salt (e.g., sodium salt, potassium salt, calcium salt, magnesium salt, etc.); ammonium salt; an organic amine salt (e.g., triethylamine salt, dicyclohexylamine salt, etc.), and the like.

Suitable reactive derivative at the carboxy group of the compound (III) may include an acid halide, an acid anhydride, an activated amide, an activated ester, and the like. The suitable example may be an acid chloride, an acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g., pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, triazole or tetrazole; or an activated ester (e.g., cyanomethyl ester, methoxymethyl ester, dimethyliminomethyl [(CH$_3$)$_2$N$^+$=CH—] ester, vinyl ester, propargyl ester, p-nitrophenyl ester, 2,4-dinitrophenyl ester, trichlorophenyl ester, pentachlorophenyl ester, mesyl phenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g., N,N-dimethylhydroxylamine, 1-hydroxy-2-(1H)-pyridone, N-hydroxysuccinimide, N-hydroxyphthalimide, 1-hydroxy-6-chloro-1H-benzotriazole, etc.), and the like. These reactive derivatives can optionally be selected from them according to the kind of the compound (III) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely influence the reaction. These conventional solvents may also be used in a mixture with water.

When the compound (III) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N-carbonylbis-(2-methyl imidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride; phosphorus trichloride; thionyl chloride; oxalyl chloride; triphenylphosphine; 2-ethyl-7-hydroxybenzisoxazolium salt; 2-ethyl-5-(m-sulfophenyl)isoxazolium hydroxide intra-molecular salt; 1-(p-chlorobenzenesulfonyloxy)-6-chloro-1H-benzotriazole; so-called Vilsmeier reagent prepared by the reaction of dimethylformamide with thionyl chloride, phosgene, phosphorus oxychloride, etc.; or the like.

The reaction may also be carried out in the presence of an inorganic or organic base such as an alkali metal bicarbonate, tri(lower)alkylamine, pyridine, N-(lower)alkylmorphorine, N,N-di(lower)alkylbenzylamine, or the like. The reaction temperature is not critical, and the reaction is usually carried out under cooling or at ambient temperature.

In the present reaction, a syn isomer of the object compound (I) can be obtained preferably by conducting the present reaction of the compound (II) with the corresponding syn isomer of the starting compound (III), for example, in the presence of a Vilsmeier reagent as mentioned above etc. and under around neutral condition.

Process 2

The object compound (Ib) or a salt thereof can be prepared by subjecting the compound (Ia) or a salt thereof to elimination reaction of the amino protective group.

Suitable salt of the compound (Ia) can be referred to the metal salt, ammonium salt and organic amine salt exemplified for the compound (II).

The elimination reaction is carried out in accordance with a conventional method such as hydrolysis; reduction; a method treating the compound (Ia) wherein $R^{1a}$ is acylamino with iminohalogenating agent, iminoetherifying agent and then, if necessary, hydrolyzing the resultant; or the like. The hydrolysis may include a method using an acid or base or hydrazine and the like. These methods may be selected depending on the kind of the protective groups to be eliminated.

Among these methods, hydrolysis using an acid is one of the most common and preferable method for eliminating the protective groups such as substituted or unsubstituted alkoxycarbonyl, for example, tert-pentyloxycarbonyl, lower alkanoyl (e.g., formyl, acetyl, etc.), cycloalkoxycarbonyl, substituted or unsubstituted aralkoxycarbonyl, aralkyl (e.g., trityl), substituted phenylthio, substituted aralkylidene, substituted alkylidene, substituted cycloalkylidene or the like. Suitable acid includes an organic or inorganic acid such as formic acid, trifluoroacetic acid, benenesulfonic acid, p-toluenesulfonic acid, hydrochloric acid and the like, and the most suitable acid is an acid which can easily be removed from the reaction mixture by a conventional manner such as distillation under reduced pressure, for example, formic acid, trifluoroacetic acid, hydrochloric acid, etc. The acids can be selected according to the kind of the protective group to be eliminated. When the elimination reaction is conducted with an acid it can be carried out in the presence or absence of a solvent. Suitable solvent includes water, a conventional organic solvent or a mixture thereof.

The elimination reaction using trifluoroacetic acid may be carried out in the presence of anisole. The hydrolysis using hydrazine is commonly applied for eliminating a phthaloyl, succinyl type aminoprotective group.

The elimination using base is used for eliminating an acyl group such as trifluoroacetyl. Suitable base may include an inorganic base and an organic base.

The reductive elimination is generally applied for eliminating the protective group, for example, haloalkoxycarbonyl (e.g., trichloroethoxycarbonyl, etc.), substituted or unsubstituted aralkoxy carbonyl (e.g., benzyloxycarbonyl, etc.), 2-pyridylmethoxycarbonyl, etc. Suitable reduction may include, for example, reduction with an alkali metal borohydride (e.g., sodium borohydride, etc.), reduction with a combination of a metal (e.g., tin, zinc, iron, etc.) or the said metal together with a metal salt compound (e.g., chromous chloride, chromous acetate, etc.) and an organic or inorganic acid (e.g., acetic acid, propionic acid, hydrochloric acid, etc.); and catalytic reduction. Suitable catalyst includes a conventional one, for example, Raney nickel, platinum oxide, palladium on charcoal and the like.

Among the protective groups, the acyl group can generally be eliminated by hydrolysis. Especially, halogen substituted-alkoxycarbonyl and 8-quinolyloxycarbonyl groups are usually eliminated by treating with a heavy metal such as copper, zinc, or the like.

Among the protective groups, the acyl group can also be eliminated by treating with an iminohalogenating agent (e.g., phosphorus oxychloride, etc.) and an iminoetherifying agent such as lower alkanol (e.g., methanol, ethanol, etc.), if necessary, followed by hydrolysis.

The reaction temperature is not critical and may suitably be selected in accordance with the kind of the protective group for the amino group and the elimination method as mentioned above, and the reaction is preferably carried out under a mild condition such as under cooling or at slightly elevated temperature.

The present invention includes, within its scope, the cases that another protected amino and/or a protected carboxy group(s) are converted into the corresponding free amino and/or the free carboxy group(s) during the reaction or the post-treating step of the present process.

Process 3

The object compound (Id) or a salt thereof can be prepared by reacting a compound (Ic) or a salt thereof with a compound (IX) or its reactive derivative.

Suitable salts of the compound (Ic) are referred to the ones exemplified for the compound (I).

Suitable reactive derivative in the compound (IX) may include a metal salt such as an alkali metal salt (e.g. sodium salt, potassium salt, etc.), an alkaline earth metal salt (e.g., magnesium salt, etc.) or the like.

The reaction may be carried out in the presence of sodium iodide, sodium thiocyanate and the like.

The reaction is usually carried out in a solvent such as water, acetone, chloroform, nitrobenzene, methylene chloride, ethylene chloride, dimethylformamide, methanol, ethanol, ether, tetrahydrofuran or any other conventional solvents which do not adversely influence the reaction, preferably in ones having strong polarity, which may be used as a mixture with water.

When the compound (Ic) and/or the compound (IX) are used in free form in the reactions, the reaction is preferably carried out in the presence of a base, for example, an organic or an inorganic base such as alkali metal hydroxide, alkali metal carbonate, alkali metal bicarbonate, trialkylamine, pyridine or the like, and preferably carried out around neutral conditions. The reaction temperature is not critical and the reaction is usually carried out at ambient temperature or under warming.

The present invention includes, within its scope, the cases that a protected amino and/or a protected carboxy group are converted into the corresponding free amino and/or the free carboxy group during the reaction or the post-treating step of the present process.

Process 4

The object compound (If) or a salt thereof can be prepared by subjecting the compound (Ie) or a salt thereof to elimination reaction of the carboxy protective group.

Suitable salt of the compound (Ie) can be referred to the acid addition salt exemplified for the compound (II).

In the present elimination reaction, all conventional methods used in the elimination reaction of the carboxy protective group, for example, hydrolysis, reduction, elimination using Lewis acid, etc. are applicable. When the carboxy protective group is an ester, it can be eliminated by hydrolysis or elimination using Lewis acid. The hydrolysis is preferably carried out in the presence of a base or an acid. Suitable base may include an inorganic base and an organic base as aforementioned.

Suitable acid may include an organic acid (e.g. formic acid, acetic acid, propionic acid, etc.) and an inorganic acid (e.g. hydrochloric acid, hydrobromic acid, sulfuric acid, etc.).

The present hydrolysis is usually carried out in an organic solvent, water or a mixed solvent thereof.

The reaction temperature is not critical, and it may suitably be selected in accordance with the kind of the protective group of the carboxy and the elimination method.

The elimination using Lewis acid is preferable to eliminate substituted or unsubstituted ar(lower)alkyl ester and carried out by reacting the compound (Ie) or a salt thereof with Lewis acid such as boron trihalide (e.g. boron trichloride, boron trifluoride, etc.), titanium tetrahalide (e.g. titanium tetrachloride, titanium tetrabromide, etc.), tin tetrahalide (e.g. tin tetrachloride, tin tetrabromide etc.), aluminum halide (e.g. aluminum chloride, aluminum bromide, etc.), trihaloacetic acid (e.g. trichloroacetic acid, trifluoroacetic acid, etc.) or the like. This elimination reaction is preferably carried out in the presence of cation trapping agents (e.g. anisole, phenol, etc.) and is usually carried out in a solvent such as nitroalkane (e.g. nitromethane, nitroethane, etc.), alkylene halide (e.g., methylene chloride, ethylene chloride, etc.), diethyl ether, carbon disulfide or any other solvent which does not adversely affect the reaction. These solvents may be used as a mixture thereof. The reaction temperature is not critical, and the reaction is usually carried out under cooling, at ambient temperature or under warming.

The reductive elimination can be applied preferably for elimination of the protective group such as halo(lower)alkyl (e.g. 2-iodoethyl, 2,2,2-trichloroethyl, etc.) ester, ar(lower)alkyl (e.g. benzyl, etc.) ester or the like. The reduction method applicable for the elimination reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, etc.); and conventional catalytic reduction in the presence of a conventional metallic catalyst (e.g. palladium carbon, Raney nickel, etc.).

The present elimination reaction of the carboxy protective group includes, within its scope, the cases that protected amino group in the compound (Ie) is transformed into free amino group according to reaction conditions and kinds of the protective groups in the course of the reaction and/or in post-treatment of the reaction.

Process 5

The object compound (Ih) or a salt thereof can be prepared by subjecting the compound (Ig) or a salt thereof to elimination reaction of the amino protective group.

Suitable salt of the compound (Ig) can be referred to the ones exemplidied for the compound (I).

This elimination reaction of the amino protective group of the compound (Ig) can be carried out in a similar manner to that of aforementioned Process 2.

Processes for the preparation of the starting compounds (II) and (III) are explained in detail as follows.

Preparation 1. (IV)+(V)→(VI): [Process (A)]

The compound (VI) can be prepared by reacting a compound (IV) with a compound (V).

The reaction is preferably carried out in the presence of a base as exemplified in Process 1 in case that X is an acid residue and in the presence of a condensing agent, for example, one formed by triphenylphosphine and diethyl azoformate in case that X is hydroxy, respectively.

The reaction is usually carried out in a solvent such as acetonitrile, dimethylformamide, tetrahydrofuran or any other solvents which do not adversely influence the reaction. The reaction temperature is not critical and the reaction is usually carried out from cooling to heating around a boiling point of the solvent used.

Preparation 2. (VI)→(VII): [Process (A)]

The compound (VII) or a salt thereof can be prepared by subjecting a compound (VI) to elimination reaction of the amino protective group.

This elimination reaction of the amino protective group of the compound (VI) can be carried out in a similar manner to that of aforementioned Process 2

Suitable solvents include water, ethanol, chloroform, diethyl ether and the like. The reaction temperature is not critical and the reaction is usually carried out under warming or heating.

Preparation 3. (VII)+(VIII)→(III): [Process (A)]

The compound (III) or a salt thereof can be prepared by reacting a compound (VII) or a salt thereof with a compound (VIII).

Suitable salts of the compound (VII) include an inorganic acid salt (e.g., hydrochloride, hydrobromide, sulfate, etc.), an organic acid salt (e.g., acetate, p-toluenesulfonate, etc.) and the like.

The reaction is usually carried out in a conventional solvent such as water, alcohol (e.g., methanol, ethanol, etc.), a mixture thereof or any other ones which do not adversely influence the reaction.

When the compound (VII) is used in its salt form, the reaction is preferably carried out in the presence of an organic or an inorganic base as exemplified before.

The reaction temperature is not critical, and the reaction is usually carried out from cooling to heating.

In the present reaction, a syn isomer of the compound (III) can be obtained preferably by conducting the present reaction under around neutral conditions.

Preparation 4: (IIIa)→(IIIb): [Process (B)]

The compound (IIIb) or a salt thereof can be prepared by subjecting the compound (IIIa) or a salt thereof to the reaction to introduce the amino protective group.

The present reaction can be carried out in a similar manner to that of aforementioned process 1.

Preparation 5. (IIb)+(IXa)→(IIa): [Process (C)]

The compound (IIa) or a salt thereof can be prepared by reacting a compound (IIb) or a salt thereof with a compound (IXa) or its reactive derivative at the mercapt group or a salt thereof.

The present reaction can be carried out in a similar manner to that of aforementioned Process 3.

The present invention includes, within its scope, the cases that the one type of tautomeric isomers is converted into the other type of isomer during the reaction and/or the post-treating step of the each process.

In case that the object compound (I) is obtained in a form of the free acid at the 4-position and/or in case that the compound (I) has free amino group, it may be transformed into its pharmaceutically acceptable salt as aforementioned by a conventional method.

The object compounds (I) and pharmaceutically acceptable salt thereof of the present invention are novel compounds which exhibit high antibacterial activity and inhibit the growth of a wide variety of pathogenic microorganisms including Gram-positive and Gram-negative bacteria. For therapeutic purpose, the compounds according to the present invention can be used in the form of pharmaceutical preparation which contain said compounds, as an active ingredient, in admixture with a pharmaceutically acceptable carriers such as an organic or inorganic solid or liquid excipient suitable for oral, parenteral or external administration. The pharmaceutical preparations may be capsules, tablets, dragees, ointments or suppositories, solutions, suspensions, emulsions, and the like. If desired, there may be included in the above preparations auxiliary substances, stabilizing agents wetting or emulsifying agents, buffers and other commonly used additives.

While the dosage of the compounds will vary depend upon the age and condition of the patient, an average single dose of about 10 mg., 50 mg., 100 mg., 250 mg., 500 mg., and 1000 mg. of the compounds according to the present invention was proved to be effective for treating infectious diseases caused by pathogenic bacteria. In general, amounts between 1 mg/body and about 6,000 mg/body or even more may be administered per day.

In order to illustrate the usefulness of the object compounds, anti-microbial activities of some representative compounds of the present invention against some test strains of pathogenic bacteria are shown in their minimal inhibitory concentrations below.

Test Method

In vitro antibacterial activity was determined by the two-fold agar-plate dilution method as described below.

One loopful of an overnight culture of each test strain in Trypticase-soy broth ($10^8$ viable cells per ml) was streaked on heart infusion agar (HI-agar) containing graded concentrations of representative test compound, and the minimal inhibitory concentration (MIC) was expressed in terms of $\mu$g/ml. after incubation at 37° C. for 20 hours.

Test compounds (1) 7-[2-(2-Cyclopenten-1-yl)oxyimino-2-(2-aminothiazol-4-yl)acetamido]-3-cephem-4-carboxylic acid (syn isomer)

(2) 7-[2-(2-Cyclopenten-1-yl)oxyimino-2-(2-aminothiazol-4-yl)acetamido]-3-(1,3,4-thiadiazol-2-yl)thiomethyl-3-cephem-4-carboxylic acid (syn isomer).

(3) 7-[2-(2-Cyclopenten-1-yl)oxyimino-2-(2-aminothiazol-4-yl)acetamido]-3-(1-allyl-1H-tetrazol-5-yl)thiomethyl-3-cephem-4-carboxylic acid (syn isomer).

(4) 7-[2-(2-Cyclohexen-1-yl)oxyimino-2-(2-aminothiazol-4-yl)acetamido]-3-cephem-4-carboxylic acid (syn isomer).

(5) N-[7-{2-(2-Cyclopenten-1-yl)oxyimino-2-(2-aminothiazol-4-yl)acetamido}-3-cephem-3-ylmethyl]-pyridinium-4-carboxylate (syn isomer).

(6) 7-[2-(2-Cyclopenten-1-yl)oxyimino-2-(2-aminothiazol-4-yl)acetamido]-3-(tetrazolo[1,5-b]-pyridazin-6-yl)thiomethyl-3-cephem-4-carboxylic acid (syn isomer).

| Test Microorganism | M.I.C. ($\mu$g/ml) | | | | | |
|---|---|---|---|---|---|---|
| | Compound (1) | Compound (2) | Compound (3) | Compound (4) | Compound (5) | Compound (6) |
| Bacillus subtilis ATCC 6633 | 3.130 | 0.390 | 0.390 | 3.130 | 0.200 | 0.390 |
| Escherichia coli 31 | 0.025 | 0.100 | 0.100 | 0.050 | 0.050 | 0.050 |
| Klebsiella pneumoniae 20 | 0.200 | 0.390 | 0.390 | 0.780 | 0.390 | 0.390 |
| Proteus mirabilis 18 | 0.200 | 0.780 | 0.780 | 0.780 | 0.780 | 0.780 |

The following preparations and examples are given for the purpose of illustrating the present invention.

Preparation 1

(1) A mixture of 3-chlorocyclopentene (36.9 g), N-hydroxyphthalimide (58.2 g) and triethylamine (53.9 g) in acetonitrile (370 ml) was refluxed for 2 hours. The reaction mixture was poured into icewater. The precipitated crystals were collected by filtration, washed with water and dried over phosphorus pentoxide to give N-(2-cyclopenten-1-yl)oxyphthalimide (56.5 g).

I.R. (Nujol): 1780, 1730, 1610 cm$^{-1}$
N.M.R. (DMSO-d$_6$,δ) 1.98–2.9 (4H, m), 5.42 (1H, s), 6.00 (1H, m), 6.28 (1H, m), 7.92 (4H, s)

(2) A mixture of 3-hydroxycyclohexene (4.0 g), N-hydroxyphthalimide (6.7 g) and triphenyl phosphine (9.2 g) in tetrahydrofuran (200 ml) was stirred at room temperature. After the addition of diethyl azoformate (7.9 g), the resulting mixture was stirred for 20 hours at room temperature. The reaction mixture was evaporated and the residue was subjected to column chromatography on silica gel (80 g), using chloroform as an eluent. The fractions containing the objected compounds were combined and evaporated to give N-(2-cyclohexen-1-yl)oxyphthalimide (6.5 g).

I.R. (Nujol): 1780, 1720 cm$^{-1}$
N.M.R. (DMSO-d$_6$,δ) 1.43–2.2 (6H, m), 4.5–4.8 (1H, m), 5.68–6.25 (2H, m), 7.48 (4H, s).

Preparation 2

(1) A mixture of N-(2-cyclopenten-1-yl)oxyphthalimide (30.0 g) and hydrazine hydrate (14.5 g) in ethanol (300 ml) was stirred for 1.5 hours at 60° C. After the addition of conc.hydrochloric acid (30 ml) and water (300 ml) to the reaction mixture, the resulting mixture was filtered and the filtrate was evaporated. The remaining mixture was filtered and to the filtrate containing (2-cyclopenten-1-yl)oxyamine hydrochloride was added ethanol (400 ml). The mixture was adjusted to pH 7.0 with 4 N aqueous solution of sodium hydroxide and thereto were added 2-(2-formamidothiazol-4-yl)glyoxylic acid (21.9 g). The resulting mixture was adjusted to pH 4–4.5 with 10% hydrochloric acid and stirred for 3 hours. The reaction mixture was evaporated, adjusted to pH 7.5 with an aqueous solution of sodium hydroxide (4 N) and washed with ethyl acetate, and then a mixture of ethyl acetate and tetrahydrofuran was added to the aqueous layer. The resulting mixture was adjusted to pH 2.0 with 10% hydrochloric acid, washed with a saturated aqueous solution of sodium chloride, dried over magnesium sulfate and concentrated. The precipitated crystals were collected by filtration, washed with diethyl ether and dried to give 2-(2-cyclopenten-1-yl)oxyimino-2-(2-formamidothiazol-4-yl)acetic acid (syn isomer) (19.0 g).

I.R. (Nujol): 3200, 1740, 1710, 1600, 1560 cm$^{-1}$
N.M.R. (DMSO-d$_6$,δ) 1.52–2.67 (4H, m), 5.45 (1H, m), 6.00 (1H, m), 6.28 (1H, m), 7.67 (1H, s), 8.73 (1H, s), 13.0 (1H, broad s)

(2) A mixture of N-(2-cyclohexen-1-yl)oxyphthalimide (6.5 g) in ethanol was warmed to 60° C. with stirring and thereto was added hydrazine hydrate (2.6 g) at the same temperature, and the stirring was continued for 1.5 hours. After the addition of conc.hydrochloric acid (8 ml) and water (80 ml) to the reaction mixture, the mixture was filtered and the filtrate was evaporated under reduced pressure. The precipitates were filtered out and the filtrate containing (2-cyclohexen-1-yl)oxyamine hydrochloride was washed with ethyl acetate and then adjusted to pH 7.0 with an aqueous solution of sodium hydroxide (4 N). To the resulting mixture were added 2-(2-formamidothiazol-4-yl)glyoxylic acid (4.6 g) and ethanol (120 ml). The mixture was adjusted to pH 4 to 4.5 with 10% hydrochloric acid and stirred for 2 hours at room temperature. The reaction mixture was adjusted to pH 7.5 with 4 N aqueous solution of sodium hydroxide and evaporated under reduced pressure. The residue was washed with ethyl acetate. To the aqueous layer was added ethyl acetate and then the pH was adjusted to 2.0 with hydrochloric acid. The organic layer was separated, washed with a saturated aqueous solution of sodium chloride, dried over magnesium sulfate and evaporated to give 2-(2-cyclohexen-1-yl)oxyimino-2-(2-formamidothiazol-4-yl)acetic acid (syn isomer) (2.3 g).

I.R. (Nujol): 3200, 1700, 1550 cm$^{-1}$
N.M.R. (DMSO-d$_6$,δ) 1.35–2.32 (6H, m), 4.52–4.9 (1H, m), 5.62–6.2 (2H, m), 7.55 (1H, s), 8.57 (1H, s), 12.7 (1H, broad s)

(3) A mixture of N-(2-cyclohexen-1-yl)oxyphthalimide (17.6 g) and hydrazine hydrate (7.2 g) in ethanol (180 ml) was stirred for 1.5 hours at 60° C. After the addition of water (100 ml) and conc.hydrochloric acid (20 ml) to the reaction mixture, the resulting mixture was filtered and the filtrate was evaporated. The remaining mixture was filtered to give the filtrate containing (2-cyclohexen-1-yl)oxyamine hydrochloride (Filtrate A). To a suspension of 2-(2-formamidothiazol-4-yl)glyoxylic acid (10.0 g) in water (50 ml) was added a solution of sodium hydroxide (4.4 g) in water (50 ml). The resulting mixture was stirred for 2.5 at room temperature and the mixture containing 2-(2-aminothiazol-4-yl)glyoxylic acid was adjusted to pH 7.0 with 10% hydrochloric acid and then thereto was added the above obtained Filtrate A. The mixture was stirred for 2 hours at room temperature. The reaction mixture was adjusted to pH 7.5 with 4 N aqueous solution of sodium hydroxide and then evaporated. The residue was washed with ethyl acetate and then adjusted to pH 2.0 with 10% hydrochloric acid. The precipitates were collected by filtration, washed with water, dried over phosphorus pentoxide to give 2-(2-cyclohexen-1-yl)oxyimino-2-(2-aminothiazol-4-yl)acetic acid (syn isomer) (2.0 g).

I.R. (Nujol): 3400–3100, 1660–1600 cm$^{-1}$
N.M.R. (DMSO-d$_6$,δ) 1.06–2.28 (6H, m), 4.60 (1H, s), 5.56–6.10 (2H, m), 6.82 (1H, s)

(4) The following compound was prepared according to a similar manner to those of Preparation 2(1)-(3)
2-(2-Cyclopenten-1-yl)oxyimino-2-(2-aminothiazol-4-yl)acetic acid (syn isomer).

N.M.R. (DMSO-d$_6$,δ) 1.47–2.88 (4H, m), 5.28 (1H, m), 5.32–5.7 (2H, m), 6.85 (1H, s)

Preparation 3

To a solution of 2-(2-cyclopenten-1-yl)oxyimino-2-(2-aminothiazol-4-yl)acetic acid (syn isomer) (2.8 g) in ethyl acetate (30 ml) was added bis(trimethylsilyl)acetamide (5.0 g) with stirring under ice-cooling. The mixture was stirred for 10 minutes at room temperature and then cooled to −10° C. 2,2,2-Trifluoroacetic anhydride (7.5 g) was dropwise added thereto, keeping the temperature at −10° C. The resulting mixture was stirred at the same temperature for 20 minutes and at 0° to 5° C. for 2 hours and then cooled to −10° C. After the addition of water (30 ml) and ethyl acetate (20 ml) to the reaction mixture, the pH was adjusted to 1.5 with a saturated aqueous solution of sodium bicarbonate. The ethyl acetate layer was separated, washed with a saturated aqueous solution of sodium chloride, dried over magnesium sulfate and then evaporated. The residue was washed with a mixture of diisopropyl ether and hexane to give 2-(2-cyclopenten-1-yl)oxyimino-2-{2-(2,2,2-trifluoroacetamido)thiazol-4-yl}acetic acid (syn isomer) (1.8 g).

I.R. (Nujol): 3400–3100, 1720, 1590 cm$^{-1}$
N.M.R. (DMSO-d$_6$,δ) 1.4–2.9 (4H, m), 5.35 (1H, m), 5.7–6.37 (2H, m), 7.65 (1H, s), 10.2 (1H, broad's)

Preparation 4

(1) To a suspension of 2-mercapto-4-pyridinecarboxylic acid (7.65 g) in a mixture of tetrahydrofuran (60 ml) and methanol (60 ml) was added a solution of sodium 2-ethylhexanoate in isopropyl alcohol (27.5%) and the mixture was stirred for 2 days at room temperature. The reaction mixture was evaporated and the residue was washed with a mixture of acetone and ethanol. The crystals were collected by filtration dried over phosphorus pentoxide to give disodium 2-sulfido-4-pyridinecarboxylate (8.5 g).

I.R. (Nujol): 1570, 1390 cm$^{-1}$
N.M.R. (D$_2$O,δ) 7.27–8.63 (3H, m)

(2) To a suspension of 7-aminocephalosporanic acid (9.30 g) and disodium 2-sulfido-4-pyridinecarboxylate (6.80 g) in water (160 ml) was dropwise added sodium bicarbonate (5.73 g) at room temperature. To the resulting mixture was added a saturated aqueous solution of sodium bicarbonate so that the pH was adjusted to 6.8. The resulting mixture was warmed to 65° C. and stirred for 1.5 hours during which period the temperature was allowed to rise from 65° to 75° C. The reaction mixture was cooled and then adjusted to pH 3.6 with 10% hydrochloric acid. The precipitates were collected by filtration, washed successively with water (x2), acetone (x2) and diethyl ether and then dried to give 7-amino-3-(4-carboxypyridin-2-yl)thiomethyl-3-cephem-4-carboxylic acid (6.61 g).

I.R. (Nujol): 1800, 1700, 1610, 1540, 1410 cm$^{-1}$
N.M.R. (DMSO-d$_6$,δ) 3.60 (2H, ABq, J=16 Hz), 4.33 (2H, ABq, J=13 Hz), 4.70–5.03 (2H, m), 7.50–7.90 (2H, m), 8.57–8.77 (1H, m)

EXAMPLE 1

The solution of Vilsmeier reagent was prepared from dry N,N-dimethylformamide (0.62 g) and phosphoryl chloride (1.3 g) in dry ethyl acetate (16 ml) in a usual manner.

A solution of 2-(2-cyclopenten-1-yl)oxyimino-2-(2-formamidothiazol-4-yl)acetic acid (syn isomer) (2.0 g) in dry tetrahydrofuran (5 ml) was added to the stirred suspension of the solution of Vilsmeier reagent under ice-cooling. The resulting mixture was added to a solution of 7-amino-3-cephem-4-carboxylic acid (1.4 g) and trimethylsilylacetamide (5.5 g) in ethyl acetate (14 ml) at −10° C. and the mixture was stirred at −5°~−10° C. for 30 minutes.

After the addition of ethyl acetate and water to the reaction mixture, the organic layer was separated, and thereto was added an aqueous solution of sodium bicarbonate. The aqueous solution was separated and thereto was added ethyl acetate. The mixture was adjusted to pH 3.0 with 10% hydrochloric acid. The organic layer was separated, washed with a saturated aqueous solution of sodium chloride, dried over magnesium sulfate and evaporated to give 7-[2-(2-cyclopenten-1-yl)oxyimino-2-(2-formamidothiazol-4-yl)acetamido]-3-cephem-4-carboxylic acid (syn isomer) (1.75 g). mp. 145° to 170° C. (dec.).

I.R. (Nujol): 3400–3100, 1780, 1680, 1650, 1540 cm$^{-1}$
N.M.R. (DMSO-d$_6$,δ) 12.6 (1H, broad s), 9.55 (1H, d, J=8 Hz), 8.5 (1H, s), 7.35 (1H, s), 6.47 (1H, m), 6.07 (1H, m), 6.25–5.68 (3H, m), 5.32 (1H, m), 5.08 (1H, d, J=5 Hz), 3.58 (2H, m), 2.67–1.57 (4H, m).

EXAMPLE 2

The solution of Vilsmeier reagent was prepared from dry N,N-dimethylformamide (0.48 g) and phosphoryl chloride (0.98 g) in dry ethyl acetate (3 ml) in a usual manner.

A solution of 2-(2-cyclopenten-1-yl)oxyimino-2-(2-formamidothiazol-4-yl)acetic acid (syn isomer) (1.5 g) in dry tetrahydrofuran (12 ml) was added to the stirred suspension of the solution of Vilsmeier reagent under ice-cooling. The resulting mixture was added to a solution of 7-amino-2-methyl-3-cephem-4-carboxylic acid (1.37 g) and trimethylsilylacetamide (5.04 g) in ethyl acetate (14 ml) at −30° to −20° C. and the mixture was stirred at −5°~−10° C. for 2 hours. After the addition of water and ethyl acetate to the reaction mixture, the ethyl acetate layer was separated and adjusted to pH 7 with an aqueous solution of sodium bicarbonate. The aqueous layer was separated and thereto was added ethyl acetate. The mixture was adjusted to pH 2.5 with 10% hydrochloric acid. The ethyl acetate layer was separated, washed with an aqueous solution of sodium chloride, dried over magnesium sulfate and then evaporated. The residue was pulverized in diisopropyl ether to give 7-[2-(2-cyclopenten-1-yl)oxyimino-2-(2-formamidothiazol-4-yl)acetamido]-2-methyl-3-cephem-4-carboxylic acid (syn isomer) (1.98 g).

I.R. (Nujol): 3260, 1780, 1680, 1660 cm$^{-1}$
N.M.R. (DMSO-d$_6$,δ)1.45 (3H, d, J=8 Hz), 1.72–1.75 (4H, m), 3.55–4.15 (1H, m), 5.15 (1H, d, J=5 Hz), 5.18–5.55 (1H, m), 5.92 (1H, dd, J=5 and 8 Hz), 5.93–6.38 (2H, m), 6.58 (1H, d, J=5 Hz), 7.4 (1H, s), 8.55 (1H, s), 9.62 (1H, d, J=8 Hz), 12.72 (1H, broad s).

EXAMPLE 3

The solution of Vilsmeier reagent was prepared from dry N,N-dimethylformamide (0.38 g) and phosphoryl chloride (0.79 g) in dry ethyl acetate (15 ml) in a usual manner.

2-2-(Cyclopenten-1-yl)oxyimino-2-[2-(2,2,2-trifluoroacetamido)thiazol-4-yl]acetic acid (syn isomer) (1.5 g) was added to the stirred suspension of the solution of Vilsmeier reagent under ice-cooling. The resulting mixture was added to a solution of 7-aminocephalosporanic acid (1.7 g) and trimethylsilylacetamide (3.4 g) in ethyl acetate (12 ml) at −10° C. and the mixture was stirred at −5°~−10° C. for 30 minutes.

After the addition of water and ethyl acetate to the reaction mixture, the ethyl acetate layer was separated and thereto was added an aqueous solution of sodium bicarbonate. The aqueous layer was separated and thereto was added ethyl acetate. The mixture was adjusted to pH 3.0 with 10% hydrochloric acid. The ethyl acetate layer was separated, washed with a saturated aqueous solution of sodium chloride, dried over magnesium sulfate and then evaporated to give 7-[2-(2-cyclopenten-1-yl)oxyimino-2-{2-(2,2,2-trifluoroacetamido)-thiazol-4-yl}acetamido]cephalosporanic acid (syn isomer) (1.8 g)

I.R. (Nujol): 3400–3100, 1780, 1730, 1660, 1580, 1510 cm$^{-1}$

N.M.R. (DMSO-d$_6$, δ) 1.5–2.73 (4H, m), 3.62 (2H, broad s), 4.9 (2H, q, J=13 Hz), 5.2 (1H, d, J=5 Hz), 5.38 (1H, m), 6.3–5.7 (3H, m), 7.53 (1H, s), 9.7 (1H, d, J=8 Hz).

EXAMPLE 4

The solution of Vilsmeier reagent was prepared from dry N,N-dimethylformamide (0.43 g) and phosphoryl chloride (0.90 g) in dry ethyl acetate (1.72 ml) in a usual manner.

A solution of 2-(2-cyclopenten-1-yl)oxyimino-2-(2-formamidothiazol-4-yl)acetic acid (syn isomer) (1.4 g) in dry ethyl acetate (20 ml) was added to the stirred suspension of the solution of Vilsmeier reagent under ice-cooling. The resulting mixture was added to a solution of 7-amino-3-(1,3,4-thiadiazol-2-yl)thiomethyl-3-cephem-4-carboxylic acid (1.5 g) and trimethylsilylacetamide (4.2 g) in dry tetrahydrofuran (30 ml) at −10° C. and the mixture was stirred at −5° ∼ −10° C. for 30 minutes.

After the addition of water to the reaction mixture, the temperature of the mixture fell back to room temperature and then the organic layer was separated. The organic layer was adjusted to pH 7.5 with an aqueous solution of sodium bicarbonate. The aqueous layer was separated, washed with ethyl acetate and then thereto were added ethyl acetate and tetrahydrofuran. The mixture was adjusted to pH 2.0 with 10% hydrochloric acid. The organic layer was separated, washed with water, dried over magnesium sulfate, treated with activated charcoal and evaporated. The residue was pulverized in diethyl ether, collected by filtration, washed with diethyl ether and then dried to give 7-[2-(2-cyclopenten-1-yl)oxyimino-2-(2-formamidothiazol-4-yl)acetamido]-3-(1,3,4-thiadiazol-2-yl)thiomethyl-3-cephem-4-carboxylic acid (syn isomer) (2.63 g).

I.R. (Nujol): 3150, 1770, 1670 cm$^{-1}$

N.M.R. (DMSO-d$_6$, δ) 1.80–2.90 (4H, m), 3.74 (2H, m), 4.49 (2H, q, J=14.0 Hz), 5.20 (1H, d, J=5.0 Hz), 5.36 (1H, m), 5.68–6.30 (3H, m), 7.43 (1H, s), 8.53 (1H, s), 9.60 (1H, s), 9.65 (1H, d, J=8.0 Hz)

EXAMPLE 5

The solution of Vilsmeier reagent was prepared from dry N,N-dimethylformamide (0.62 g) and phosphoryl chloride (1.3 g) in dry ethyl acetate (16 ml) in a usual manner.

A solution of 2-(2-cyclopenten-1-yl)oxyimino-2-(2-formamidothiazol-4-yl)acetic acid (syn isomer)(2.0 g) in dry tetrahydrofuran (5 ml) was added to the stirred suspension of the solution of Vilsmeier reagent under ice-cooling. The resulting mixture was added to a solution of 7-amino-3-(1-allyl-1H-tetrazol-5-yl)thiomethyl-3-cephem-4-carboxylic acid (2.5 g) and trimethylsilylacetamide (5.5 g) in ethyl acetate (25 ml) at −10° C. and the mixture was stirred at −5° ∼ −10° C. for 30 minutes.

After the addition of water, ethyl acetate and tetrahydrofuran to the reaction mixture, the organic layer was separated and thereto was added an aqueous solution of sodium bicarbonate. The aqueous layer was separated and thereto was added ethyl acetate. The mixture was adjusted to pH 3.0 with 10% hydrochloric acid. The organic layer was separated, washed with a saturated aqueous solution of sodium chloride, dried over magnesium sulfate and evaporated to give 7-[2-(2-cyclopenten-1-yl)oxyimino-2-(2-formamidothiazol-4-yl)acetamido]-3-(1-allyl-1H-tetrazol-5-yl)thiomethyl-3-cephem-4-carboxylic acid (syn isomer)(3.25 g). mp. 120° to 139° C. (dec.).

I.R. (Nujol): 3400–3100, 1770, 1670, 1540 cm$^{-1}$

N.M.R. (DMSO-d$_6$, δ) 1.57–2.73 (4H, m), 3.73 (2H, broad s), 4.4 (2H, m), 4.88–5.52 (6H, m), 5.7–6.58 (4H, m), 7.42 (1H, s), 8.57 (1H, s), 9.63 (1H, d, J=8 Hz), 12.4 (1H, broad s)

EXAMPLE 6

The solution of Vilsmeier reagent was prepared from dry N,N-dimethylformamido (0.475 g) and phosphoryl chloride (0.997 g) in dry tetrahydrofuran (1 ml) in a usual manner.

A solution of 2-(2-cyclopenten-1-yl)oxyimino-2-(2-formamidothiazol-4-yl)acetic acid (syn isomer)(1.91 g) in dry tetrahydrofuran (12 ml) was added to the stirred suspension of the solution of Vilsmeier reagent at 0° to 5° C. and the mixture was stirred for 20 minutes. The resulting mixture was added to a solution of 7-amino-3-(4-carboxypyridin-2-yl)thiomethyl-3-cephem-4-carboxylic acid (1.84 g) and sodium bicarbonate (0.84 g) in a mixture of acetone (12 ml) and water (12 ml) at −3° to 0° C. and the mixture was stirred at the same temperature for 40 minutes.

The reaction mixture was evaporated under reduced pressure. The residue was adjusted to pH 6.5 with 10% hydrochloric acid, washed with ethyl acetate, concentrated to a small volume and then adjusted to pH 2.9 with 10% hydrochloric acid. The precipitates were collected by filtration, washed with water and dried over phosphorus pentoxide to give 7-[2-(2-cyclopenten-1-yl)oxyimino-2-(2-formamidothiazol-4-yl)acetamido]-3-(4-carboxypyridin-2-yl)thiomethyl-3-cephem-4-carboxylic acid (syn isomer)(2.74 g).

I.R. (Nujol): 1770, 1690–1650, 1540 cm$^{-1}$

N.M.R. (DMSO-d$_6$, δ) 1.73–2.50 (4H, m), 3.60 (2H, m), 4.30 (2H, ABq, J=12 Hz), 5.07–5.43 (2H, m), 5.77–6.20 (3H, m), 7.40–7.97 (4H, m), 8.53 (1H, s), 9.63 (1H, d, J=8 Hz), 12.70 (1H, broad s)

EXAMPLE 7

The solution of Vilsmeier reagent was prepared from dry N,N-dimethylformamide (0.6 g) and phosphoryl chloride (1.25 g) in dry ethyl acetate (16 ml) in a usual manner.

2-(2-Cyclohexen-1-yl)oxyimino-2-(2-formamidothiazol-4-yl)acetic acid (syn isomer)(2.0 g) was added to the stirred suspension of the solution of Vilsmeier reagent under ice-cooling. The resulting mixture was added to a solution of 7-amino-3-(1-carboxymethyl-1H-tetrazol-5-yl)thiomethyl-3-cephem-4-carboxylic acid (2.5 g) and sodium bicarbonate (2.2 g) in a mixture of acetone (25 ml) and water (25 ml) at −10° C. and the mixture was stirred at −5° ∼ −10° C. for 30 minutes.

After the addition of ethyl acetate to the reaction mixture, the aqueous layer was separated and thereto was added ethyl acetate. The mixture was adjusted to pH 3.0 with 10% hydrochloric acid. The organic layer was separated, washed with a saturated aqueous solution of sodium chloride, dried over magnesium sulfate and then evaporated to give 7-[2-(2-cyclohexen-1-yl)oxyimino-2-(2-formamidothiazol-4-yl)acetamido]-3-(1-carboxymethyl-1H-tetrazol-5-yl)thiomethyl-3-cephem-4-carboxylic acid (syn isomer)(2.0 g).

I.R. (Nujol): 3400–3100, 1700, 1670, 1540 cm$^{-1}$

N.M.R. (DMSO-d$_6$, δ) 12.7 (1H, broad s), 9.65 (1H, d, J=8 Hz), 8.53 (1H, s), 7.38 (1H, s), 6.17–5.58 (3H, m), 5.3 (2H, s), 5.12 (1H, d, J=5 Hz), 4.63 (1H, m), 4.35 (2H, q, J=13 Hz), 3.67 (2H, m), 2.42–1.13 (6H, m)

EXAMPLE 8

The solution of Vilsmeier reagent was prepared from dry N,N-dimethylformamide (0.48 g) and phosphoryl chloride (1.0 g) in dry ethyl acetate (15 ml) in a usual manner.

2-(2-Cyclohexen-1-yl)oxyimino-2-(2-formamidothiazol-4-yl)acetic acid (syn isomer)(1.5 g) was added to the stirred suspension of the solution of Vilsmeier reagent under ice-cooling. The resulting mixture was added to a solution of 7-amino-3-(1H-tetrazol-5-yl)thiomethyl-3-cephem-4-carboxylic acid (1.6 g) and trimethylsilylacetamide (4.6 g) and bis(trimethylsilyl)acetamide (3.1 g) in ethyl acetate (32 ml) at $-10°$ C. and the mixture was stirred at $-5°\sim -10°$ C. for 30 minutes.

After the addition of water and ethyl acetate to the reaction mixture, the organic layer was separated and thereto was added an aqueous solution of sodium bicarbonate. The aqueous layer was separated and thereto was added ethyl acetate. The mixture was adjusted to pH 3.0 with 10% hydrochloric acid. The organic layer was separated, washed with a saturated aqueous solution of sodium chloride, dried over magnesium sulfate and then evaporated to give 7-[2-(2-cyclohexen-1-yl)oxyimino-2-(2-formamidothiazol-4-yl)acetamido]-3-(1H-tetrazol-5-yl)thiomethyl-3-cephem-4-carboxylic acid (syn isomer) (1.7 g).

I.R. (Nujol): 3400–3100, 1770, 1660, 1540 cm$^{-1}$

N.M.R. (DMSO-d$_6$, δ) 9.63 (1H, d, J=8 Hz), 8.55 (1H, s), 7.4 (1H, s), 6.17–5.6 (3H, m), 5.18 (1H, d, J=5 Hz), 4.68 (1H, m), 4.37 (2H, m), 3.73 (2H, broad s), 2.33–1.17 (6H, m)

EXAMPLE 9

A solution of 2-(2-cyclohexen-1-yl)oxyimino-2-(2-aminothiazol-4-yl)acetic acid (syn isomer)(1.91 g: This material contains 8% of water) in tetrahydrofuran (20 ml) was stirred at below 5° C. To the solution was added phosphoryl chloride (1.4 g) and the stirring was continued for 20 minutes at below 5° C. To the solution was added trimethylsilylacetamide (1.11 g: This reagent contains 8% of water) and the stirring was continued for 20 minutes at the same temperature. And to the solution was added phosphoryl chloride (1.4 g) and the stirring was continued for 20 minutes at the same temperature. To the resulting solution was added N,N-dimethylformamide (0.65 g) and the stirring was continued for additional 30 minutes to give the solution A. A solution of 7-aminocephalosporanic acid (1.9 g) and trimethylsilylacetamide (5.6 g) in ethyl acetate (40 ml) was stirred for 15 minutes at 40° C. and then cooled to $-25°$ C. To the resulting solution was added the above obtained solution A and then the mixture was stirred for an hour at $-15°$ C. After the addition of ethyl acetate and water to the reaction mixture, the organic layer was separated, washed with a saturated aqueous solution of sodium chloride, dried over magnesium sulfate and then evaporated. The residue was adjusted to pH 6.5 with a saturated aqueous solution of sodium bicarbonate and subjected to column chromatography on alumina using 5% sodium acetate as an eluent to give 7-[2-(2-cyclohexen-1-yl)oxyimino-2-(2-aminothiazol-4-yl)acetamido]cephalosporanic acid (syn isomer)(0.5 g).

I.R. (Nujol): 3400–3100, 1770, 1740, 1660, 1630, 1520 cm$^{-1}$

N.M.R. (DMSO-d$_6$, δ) 1.28–2.25 (6H, m), 2.05 (3H, s), 3.60 (2H, broad s), 4.71 (1H, m), 4.88 (2H, m), 5.17 (1H, d, J=5 Hz), 5.65–6.22 (3H, m), 6.75 (1H, s), 9.58 (1H, d, J=8 Hz)

EXAMPLE 10

The solution of Vilsmeier reagent was prepared from dry N,N-dimethylformamide (0.4 g), phosphoryl chloride (0.8 ) and dry ethyl acetate (1.6 ml) in a usual manner. To the solution were added dry tetrahydrofuran (18 ml) and 2-(2-cyclopenten-1-yl)oxyimino-2-(2-formamidothiazol-4-yl)acetic acid (syn isomer) (1.2 g) and then stirred at $-3°$ to 3° C. (Solution A). A mixture of 7-amino-3-(tetrazolo[1,5-b]pyridazin-6-yl)thiomethyl-3-cephem-4-carboxylic acid (1.5 g), sodium carbonate (0.9 g) and water (9.0 ml) was stirred to give a homogeneous solution. After the addition of acetone (9.0 ml), the solution was cooled to $-3°$ C. and then thereto was added Solution A over a period of 5 minutes, keeping the temperature at $-3°$ to 3° C. and the pH at 7.5 to 8.5 with triethyl amine. The resulting mixture was stirred for 30 minutes at the same temperature and pH. To the reaction mixture were added water, ethyl acetate and tetrahydrofuran. The resulting mixture was adjusted to pH 2.0 with 10% hydrochloric acid and filtered. The organic layer was separated from the filtrate, washed with water (×3), dried over magnesium sulfate, treated with activated charcoal and then evaporated. The residue was pulverized in isopropyl ether. The powder was collected by filtration, washed with isopropyl ether and then dried to give 7-[2-(2-cyclopenten-1-yl)oxyimino-2-(2-formamidothiazol-4-yl)acetamido]-3-(tetrazolo[1,5-b]pyridazin-6-yl)thiomethyl-3-cephem-4-carboxylic acid (syn isomer)(1.83 g).

I.R. (Nujol): 3180, 1780, 1670 cm$^{-1}$

N.M.R. (DMSO-d$_6$, δ): 1.60–2.68 (4H, m), 3.75 (2H, ABq, J=18.0 Hz), 4.43 (2H, ABq, J=14.0 Hz), 5.17 (1H, d, J=5.0 Hz), 5.28 (1H, m), 5.72–6.22 (3H, m), 7.37 (1H, s), 7.70 (1H, d, J=9.0 Hz), 8.48 (1H, s), 8.52 (1H, d, J=9.0 Hz), 9.58 (1H, d, J=8.0 Hz), 12.57 (1H, broad s)

EXAMPLE 11

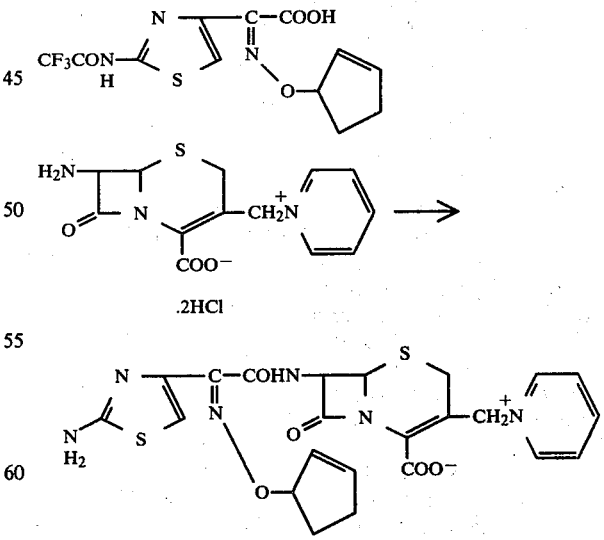

The solution of Vilsmeier reagent was prepared from dry N,N-dimethylformamide (0.48 g), phosphoryl chloride (1.0 g), ethyl acetate (4 ml) and tetrahydrofuran (15 ml) in a usual manner. To the solution was added 2-(2-cyclopenten-1-yl)oxyimino-2-[2-(2,2,2-trifluoroacetamido)thiazol-4-yl]acetic acid (syn isomer)(1.9 g) under ice cooling and the resulting solution was stirred for 30 minutes (Solution A). A mixture of N-[7-amino-3-cephem-3-ylmethyl]pyridinium-4-carboxylate dihydrochloride (2.0 g), trimethylsilylacetamide (5.7 g) and tetrahydrofuran (40 ml) was warmed to 40° C. and stirred to give a homogeneous solution, which was cooled to −25° C. and then thereto was added Solution A. The resulting mixture was stirred for 30 minutes around −10° C. To the reaction mixture containing N-[7-[2-(2-cyclopenten-1-yl)oxyimino-2-{2-(2,2,2-trifluoroacetamido)thiazol-4-yl}acetamido]-3-cephem-3-ylmethyl]pyridinium-4-carboxylate (syn isomer) were added ethyl acetate (50 ml) and water (100 ml). The ethyl acetate layer was separated and extracted with a saturated aqueous solution of sodium bicarbonate (50 ml). The extract and the remaining aqueous layer was combined, adjusted to pH 6.0 with 4 N aqueous solution of sodium hydroxide and then thereto was added sodium acetate (7.5 g). The mixture was stirred for 41 hours at room temperature, adjusted to pH 2.0 with 10% hydrochloric acid, and then filtered. The filtrate was subjected to column chromatography (non-ion adsorption resin, Diaion HP20 prepared by Mitsubishi Chemical Industries)(60 ml) and the column was washed with water and then eluted with 10% isopropyl alcohol and 30% methanol. The eluates containing the object compound were collected, evaporated and lyophilized. The obtained powder was dried over phosphorous pentoxide under reduced pressure to give N-[7-{2-(2-cyclopenten-1-yl)oxyimino-2-(2-aminothiazol-4-yl)acetamido}-3-cephem-3-ylmethyl]pyridinium-4-carboxylate (syn isomer)(0.3 g). mp. 171° to 180° C. (dec.).

I.R. (Nujol): 3400–3100, 1770, 1660, 1610, 1530 cm$^{-1}$

N.M.R. (D$_2$O, δ): 1.5–2.67 (4H, m), 3.42 (2H, ABq, J=18 Hz), 5.12–5.7 (1H, m), 5.25 (1H, d, J=5 Hz), 5.5 (2H, m), 5.85 (1H, d, J=5 Hz), 6.05 (2H, m), 6.93 (1H, s), 7.8–8.82 (3H, m), 8.98 (2H, m)

EXAMPLE 12

The following compounds were prepared according to a similar manner to those of Example 1 to 11.

(1) 7-[2-(2-Cyclopenten-1-yl)oxyimino-2-(2-formamidothiazol-4-yl)acetamido]-3-carbamoyloxymethyl-3-cephem-4-carboxylic acid (syn isomer).

I.R. (Nujol): 3450, 3260, 1770, 1660, 1640, 1700 1610, 1550 cm$^{-1}$

N.M.R. (DMSO-d$_6$, δ) 1.64–2.44 (4H, m), 3.48 (2H, q, J=17 Hz), 4.72 (2H, q, J=13 Hz), 5.12 (1H, d, J=5 Hz), 5.30 (1H, m), 6.2–5.58 (3H, m), 6.54 (2H, s), 7.36 (1H, s), 8.48 (1H, s), 9.54 (1H, d, J=8 Hz), 11.5 (1H, broad s)

(2) Benzhydryl-7-[2-(2-cyclopenten-1-yl)oxyimino-2-(2-formamidothiazol-4-yl)acetamido]-3-(2-tert-butoxycarboxamidoethyl)thiomethyl-3-cephem-4-carboxylate (syn isomer)

I.R. (Nujol): 3270, 3150, 1780, 1710, 1680, 1660, 1570, 1225 cm$^{-1}$

N.M.R. (DMSO-d$_6$, δ) 1.37 (9H, s), 1.07–2.67 (4H, m), 3.03 (2H, m), 3.33–3.87 (4H, m), 5.27 (1H, d, J=5 Hz), 5.33 (1H, m), 5.70–6.33 (5H, m), 6.97 (1H, s), 7.07–7.67 (11H, m), 8.53 (1H, s), 9.63 (1H, d, J=8 Hz), 12.72 (1H, broad s)

(3) 7-[2-(2-Cyclopenten-1-yl)oxyimino-2-(2-formamidothiazol-4-yl)acetamido]-3-(5-methyl-1,3,4-thiadiazol-2-yl)thiomethyl-3-cephem-4-carboxylic acid (syn isomer).

I.R. (Nujol): 3240, 1765, 1660 cm$^{-1}$

N.M.R. (DMSO-d$_6$, δ) 1.74–2.88 (4H, m), 2.70 (3H, s), 3.70 (2H, m), 4.40 (2H, q, J=14), 5.17 (1H, d, J=5 Hz), 5.2–5.7 (1H, m), 5.82 (1H, dd, J=5 and 8 Hz), 5.87–6.3 (2H, m), 7.4 (1H, s), 8.54 (1H, s), 9.57 (1H, d, J=8 Hz), 12.71 (1H, broad s)

(4) 7-[2-(2-Cyclopenten-1-yl)oxyimino-2-(2-formamidothiazol-4-yl)acetamido]-3-(1-methyl-1H-tetrazol-5-yl)thiomethyl-3-cephem-4-carboxylic acid (syn isomer).

I.R. (Nujol): 3240, 1760, 1670 cm$^{-1}$

N.M.R. (DMSO-d$_6$, δ) 1.6–2.93 (4H, m), 3.70 (2H, m), 3.93 (3H, s), 4.33 (2H, m), 5.15 (1H, d, J=5 Hz), 5.13–5.7 (1H, m), 5.81 (1H, dd, J=5 and 8 Hz), 5.9–6.31 (2H, m), 7.4 (1H, s), 8.5 (1H, s), 9.58 (1H, d, J=8 Hz) 12.7 (1H, broad s)

(5) 7-[2-(2-Cyclopenten-1-yl)oxyimino-2-(2-formamidothiazol-4-yl)acetamido]-3-(1-carboxymethyl-1H-tetrazol-5-yl)thiomethyl-3-cephem-4-carboxylic acid (syn isomer).

I.R. (Nujol): 3150, 1770, 1660 cm$^{-1}$

N.M.R. (DMSO-d$_6$, δ) 1.57–2.75 (4H, m), 3.72 (2H, m), 4.40 (2H, q, J=14 Hz), 5.03–5.62 (4H, m), 5.66–6.40 (3H, m), 7.41 (1H, s), 8.54 (1H, s), 9.63 (1H, d, J=8.0 Hz)

(6) 7-[2-(2-Cyclopenten-1-yl)oxyimino-2-(2-formamidothiazol-4-yl)acetamido]-3-(1H-tetrazol-5-yl)thiomethyl-3-cephem-4-carboxylic acid (syn isomer)

I.R. (Nujol): 1770, 1660 cm$^{-1}$

N.M.R. (DMSO-d$_6$, δ) 1.60–2.70 (4H, m), 3.67 (2H, m), 4.31 (2H, q, J=13.0 Hz), 5.02–5.53 (2H, m), 5.69–6.29 (3H, m), 7.39 (1H, s), 8.53 (1H, s), 9.62 (1H, d, J=8.0 Hz)

(7) 7-[2-(2-Cyclopenten-1-yl)oxyimino-2-(2-formamidothiazol-4-yl)acetamido]-3-(5-tert-butoxycarboxamidomethyl-1,3,4-thiadiazol-2-yl)thiomethyl-3-cephem-4-carboxylic acid (syn isomer). mp. 195° to 220° C. (dec.).

I.R. (Nujol): 3270, 1780, 1700, 1680, 1530 cm$^{-1}$

N.M.R. (DMSO-d$_6$, δ) 1.55 (9H, s), 1.93–2.57 (4H, m), 3.67 (2H, m), 4.2–4.67 (4H, m), 5.13 (1H, d, J=5 Hz), 5.3 (1H, m), 5.63–6.20 (3H, m), 7.37 (1H, s), 8.5 (1H, s), 9.62 (1H, d, J=8 Hz), 12.67 (1H, broad s)

(8) 7-[2-(2-Cyclohexen-1-yl)oxyimino-2-(2-formamidothiazol-4yl)acetamido]-3-cephem-4-carboxylic acid (syn isomer). mp. 155° to 185° C. (dec.).

I.R. (Nujol): 3400–3100, 1780, 1690, 1660, 1630, 1540 cm$^{-1}$

N.M.R. (DMSO-d$_6$, δ) 1.27–2.33 (6H, m), 3.62 (2H, m), 4.48–4.98 (1H, m), 5.12 (1H, d, J=5 Hz), 5.62–6.23 (3H, m), 6.48 (1H, m), 7.37 (1H, s), 8.5 (1H, s), 9.58 (1H, d, J=8 Hz), 12.6 (1H, broad s)

(9) 7-[2-(2-Cyclohexen-1-yl)oxyimino-2-(2-formamidothiazol-4-yl)acetamido]-2-methyl-3-cephem-4-carboxylic acid (syn isomer).

I.R. (Nujol): 3275, 3175, 1780, 1690, 1660, 1620, 1570, 1530 cm$^{-1}$

N.M.R. (DMSO-d$_6$, δ) 1.45 (3H, d, J=7 Hz), 1.15–2.38 (6H, m), 3.5–4.23 (1H, m), 4.67 (1H, m), 5.12 (1H, d, J=5 Hz), 6.33–5.45 (3H, m), 6.53 (1H, d, J=6 Hz), 7.33 (1H, s), 8.48 (1H, s), 9.55 (1H, d, J=8 Hz), 12.5 (1H, broad s)

(10) 7-[2-(2-Cyclohexen-1-yl)oxyimino-2-(2-formamidothiazol-4-yl)acetamido]-3-(1,3,4-thiadiazol-2-yl)thiomethyl-3-cephem-4-carboxylic acid (syn isomer).

I.R. (Nujol): 3300–3100, 1780, 1670, 1540 cm$^{-1}$

N.M.R. (DMSO-d$_6$, δ) 1.4–2.26 (6H, m), 3.7 (2H, broad s), 4.43 (2H, q, J=13 Hz), 4.43–4.83 (1H, m), 5.17 (1H, d, J=5 Hz), 5.33–6.23 (3H, m), 7.37 (1H, s), 8.5

(1H, s), 9.53 (1H, s), 9.57 (1H, d, J=8 Hz), 12.6 (1H, broad s).

(11) 7-[2-(2-Cyclohexen-1-yl)oxyimino-2-(2-formamidothiazol-4-yl)acetamido]-3-(1-methyl-1H-tetrazol-5-yl)thiomethyl-3-cephem-4-carboxylic acid (syn isomer).

I.R. (Nujol): 3400–3100, 1780, 1660, 1550 cm$^{-1}$

N.M.R. (DMSO-d$_6$, δ) 1.12–2.28 (6H, m), 3.73 (2H, broad s), 3.97 (3H, s), 4.35 (2H, m), 4.7 (1H, broad s), 5.18 (1H, d, J=5 Hz), 6.2–5.55 (3H, m), 7.42 (1H, s), 8.55 (1H, s), 9.65 (1H, d, J=8 Hz), 12.7 (1H, broad s)

(12) 7-[2-(2-Cyclohexen-1-yl)oxyimino-2-(2-formamidothiazol-4-yl)acetamido]-3-(1-allyl-1H-tetrazol-5-yl)thiomethyl-3-cephem-4-carboxylic acid (syn isomer).

I.R. (Nujol): 3400–3100, 1770, 1670, 1540 cm$^{-1}$

N.M.R. (DMSO-d$_6$, δ) 1.12–2.3 (6H, m), 3.6 (2H, broad s), 4.42 (2H, m), 4.65 (1H, m), 4.82–5.48 (5H, m), 5.57–6.47 (4H, m), 7.38 (1H, s), 8.53 (1H, s), 9.6 (1H, d, J=8 Hz), 12.4 (1H, broad s)

(13) 7-[2-(2-Cyclopenten-1-yl)oxyimino-2-(2-aminothiazol-4-yl)acetamido]-3-cephem-4-carboxylic acid (syn isomer). mp. 201° to 213° C. (dec.).

I.R. (Nujol): 3400–3100, 1770, 1650, 1620, 1540 cm$^{-1}$

(14) 7-[2-(2-Cyclopenten-1-yl)oxyimino-2-(2-aminothiazol-4-yl)acetamido]-2-methyl-3-cephem-4-carboxylic acid (syn isomer).

I.R. (Nujol): 3300, 1770, 1660, 1630 cm

(15) 7-[2-(2-Cyclopenten-1-yl)oxyimino-2-(2-aminothiazol-4-yl)acetamido]cephalosporanic acid (syn isomer). mp. 141° to 150° C. (dec.).

I.R. (Nujol): 3400–3100, 1770, 1730, 1650, 1530 cm$^{-1}$

(16) 7-[2-(2-Cyclopenten-1-yl)oxyimino-2-(2-aminothiazol-4-yl)acetamido]-3-carbamoyloxymethyl-3-cephem-4-carboxylic acid (syn isomer). mp. 182° to 195° C. (dec.).

I.R. (Nujol): 3250, 1760, 1700, 1650, 1540 cm$^{-1}$

(17) Benzhydryl 7-[2-(2-cyclopenten-1-yl)oxyimino-2-(2-aminothiazol-4-yl)acetamido]-3-(2-tert-butoxycarboxamidoethyl)thiomethyl-3-cephem-4-carboxylate (syn isomer).

I.R. (Nujol): 3500–3200, 1780, 1680, 1620 cm 1530 cm$^{-1}$

(18) 7-[2-(2-Cyclopenten-1-yl)oxyimino-2-(2-aminothiazol-4-yl)acetamido]-3-(2-aminoethyl)thiomethyl-3-cephem-4-carboxylic acid (syn isomer).

I.R. (Nujol): 3350–3100, 1760, 1660, 1610, 1515 cm$^{-1}$

(19) 7-[2-(2-Cyclopenten-1-yl)oxyimino-2-(2-aminothiazol-4-yl)acetamido]-3-(1,3,4-thiadiazol-2-yl)thiomethyl-3-cephem-4-carboxylic acid (syn isomer). mp. 152° to 157° C. (dec.).

I.R. (Nujol): 3340, 1775, 1655 cm$^{-1}$

(20) 7-[2-(2-Cyclopenten-1-yl)oxyimino-2-(2-aminothiazol-4-yl)acetamido]-3-(5-methyl-1,3,4-thiadiazol-2-yl)thiomethyl-3-cephem-4-carboxylic acid (syn isomer). mp. 148° to 152° C.

I.R. (Nujol): 3260, 1770, 1650 cm$^{-1}$

(21) 7-[2-(2-Cyclopenten-1-yl)oxyimino-2-(2-aminothiazol-4-yl)acetamido]-3-(1-methyl-1H-tetrazol-5-yl)thiomethyl-3-cephem-4-carboxylic acid (syn isomer). mp. 147° to 150° C.

I.R. (Nujol): 3300, 1770, 1660 cm$^{-1}$

(22) 7-[2-(2-Cyclopenten-1-yl)oxyimino-2-(2-aminothiazol-4-yl)acetamido]-3-(1-allyl-1H-tetrazol-5-yl)thiomethyl-3-cephem-4-carboxylic acid (syn isomer). mp. 145° to 153° C. (dec.).

I.R. (Nujol): 3400–3100, 1770, 1670, 1620, 1520 cm$^{-1}$

(23) 7-[2-(2-Cyclopenten-1-yl)oxyimino-2-(2-aminothiazol-4-yl)acetamido]-3-(1-carboxymethyl-1H-tetrazol-5-yl)thiomethyl-3-cephem-4-carboxylic acid (syn isomer). mp. 164° to 170° C. (dec.).

I.R. (Nujol): 3280, 1765, 1655 cm$^{-1}$

(24) 7-[2-(2-Cyclopenten-1-yl)oxyimino-2-(2-aminothiazol-4-yl)acetamido]-3-(4-carboxypyridin-2-yl)thiomethyl-3-cephem-4-carboxylic acid (syn isomer). mp. 174° to 205° C. (dec.).

I.R. (Nujol): 1760, 1670, 1620, 1450, 1370, 1360 cm$^{-1}$

(25) 7-[2-(2-Cyclopenten-1-yl)oxyimino-2-(2-aminothiazol-4-yl)acetamido]-3-(1H-tetrazol-5-yl)thiomethyl-3-cephem-4-carboxylic acid (syn isomer). mp. 165° to 172° C. (dec.).

I.R. (Nujol): 3300, 1770, 1660, 1630 cm$^{-1}$

(26) 7-[2-(2-Cyclopenten-1-yl)oxyimino-2-(2-aminothiazol-4-yl)acetamido]-3-(5-aminomethyl-1,3,4-thiadiazol-2-yl)thiomethyl-3-cephem-4-carboxylic acid (syn isomer). mp. 145° to 170° C. (dec.).

I.R. (Nujol): 3150, 1760, 1650, 1610, 1520 cm$^{-1}$

(27) 7-[2-(2-Cyclohexen-1-yl)oxyimino-2-(2-aminothiazol-4-yl)acetamido]-3-cephem-4-carboxylic acid (syn isomer). mp. 220° to 241° C. (dec.).

I.R. (Nujol): 3400–3100, 1770, 1650, 1630, 1530 cm$^{-1}$

(28) 7-[2-(2-Cyclohexen-1-yl)oxyimino-2-(2-aminothiazol-4-yl)acetamido]-2-methyl-3-cephem-4-carboxylic acid (syn isomer). mp. 159° to 166° C. (dec.).

I.R. (Nujol): 3400–3100, 1660, 1630, 1520 cm$^{-1}$

(29) 7-[2-(2-Cyclohexen-1-yl)oxyimino-2-(2-aminothiazol-4-yl)acetamido]-3-(1,3,4-thiadiazol-2-yl)thiomethyl-3-cephem-4-carboxylic acid (syn isomer).

I.R. (Nujol): 3400–3100, 1770, 1660, 1620, 1530 cm$^{-1}$

(30) 7-[2-(2-Cyclohexen-1-yl)oxyimino-2-(2-aminothiazol-4-yl)acetamido]-3-(1-methyl-1H-tetrazol-5-yl)thiomethyl-3-cephem-4-carboxylic acid (syn isomer). mp. 156° to 160° C. (dec.).

I.R. (Nujol): 3400–3100, 1770, 1660, 1620, 1520 cm$^{-1}$

(31) 7-[2-(2-Cyclohexen-1-yl)oxyimino-2-(2-aminothiazol-4-yl)acetamido]-3-(1-allyl-1H-tetrazol-5-yl)thiomethyl-3-cephem-4-carboxylic acid (syn isomer). mp. 148° to 157° C. (dec.).

I.R. (Nujol): 3400–3100, 1770, 1670, 1620, 1520 cm$^{-1}$

(32) 7-[2-(2-Cyclohexen-1-yl)oxyimino-2-(2-aminothiazol-4-yl)acetamido]-3-(1-carboxymethyl-1H-tetrazol-5-yl)thiomethyl-3-cephem-4-carboxylic acid (syn isomer). mp. 166° to 182° C. (dec.).

I.R. (Nujol): 3400–3100, 1770, 1660, 1620, 1530 cm$^{-1}$

(33) 7-[2-(2-Cyclohexen-1-yl)oxyimino-2-(2-aminothiazol-4-yl)acetamido]-3-(1H-tetrazol-5-yl)thiomethyl-3-cephem-4-carboxylic acid (syn isomer).

I.R. (Nujol): 3400–3100, 1770, 1660, 1630, 1520 cm$^{-1}$

(34) 7-[2-(2-Cyclopenten-1-yl)oxyimino-2-(2-formamidothiazol-4-yl)acetamido-3-[1-(2-hydroxyethyl)-1H-tetrazol-5-yl]thiomethyl-3-cephem-4-carboxylic acid (syn isomer).

I.R. (Nujol): 3400–3100, 1780, 1670, 1540 cm$^{-1}$

N.M.R. (DMSO-d$_6$, δ) 1.47–2.65 (4H, m), 3.33–3.97 (4H, m), 4.03–4.65 (4H, m), 5.13 (1H, d, J=5 Hz), 5.35 (1H, m), 5.72–6.28 (3H, m), 7.4 (1H, s), 9.60 (1H, d, J=8 Hz), 12.7 (1H, broad s)

(35) 7-[2-(2-Cyclopenten-1-yl)oxyimino-2-(2-aminothiazol-4-yl)acetamido]-3-[1-(2-hydroxyethyl)-1H-tetrazol-5-yl]thiomethyl-3-cephem-4-carboxylic acid (syn isomer). mp. 162° to 168° C. (dec.).

I.R. (Nujol): 3400–3100, 1770, 1720, 1650, 1540 cm$^{-1}$

(36) 7-[2-(2-Cyclopenten-1-yl)oxyimino-2-(2-formamidothiazol-4-yl)acetamido]-3-[1-(2-carboxyethyl)-1H-tetrazol-5-yl]thiomethyl-3-cephem-4-carboxylic acid (syn isomer).

I.R. (Nujol): 3160, 1770, 1660 cm$^{-1}$

N.M.R. (DMSO-d$_6$,δ): 1.58–2.73 (4H, m), 2.96 (2H, t, J=7.0 Hz), 3.74 (2H, ABq, J=15.0 Hz), 4.05–4.75 (4H, m), 5.16 (1H, d, J=5.0 Hz), 5.35 (1H, m), 5.66–6.30 (3H, m), 7.42 (1H, s), 8.55 (1H, s), 9.62 (1H, d, J=8.0 Hz)

(37) 7-[2-(2-Cyclopenten-1-yl)oxyimino-2-{2-(2,2,2-trifluoroacetamido)thiazol-4-yl}acetamido]-3-(1H-1,2,3-triazol-5-yl)thiomethyl-3-cephem-4-carboxylic acid (syn isomer).

I.R. (Nujol): 3250, 1780, 1730, 1660, 1590, 1540 cm$^{-1}$

N.M.R. (DMSO-d$_6$,δ): 2.10 (2H, m), 2.33 (2H, m), 3.67 (2H, m), 3.97 (2H, m), 5.17 (1H, d, J=5 Hz), 5.33 (1H, m), 5.57–6.23 (2H, m), 7.50 (1H, s), 7.90 (1H, s), 9.73 (1H, d, J=8 Hz).

(38) 7-[2-(2-Cyclopenten-1-yl)oxyimino-2-(2-formamidothiazol-4-yl)acetamido]-3-[1-{3-(N-tert-butoxycarbonylamino)propyl}-1H-tetrazol-5-yl]thiomethyl-3-cephem-4-carboxylic acid (syn isomer)

I.R. (Nujol): 3180, 1780, 1680 cm$^{-1}$

N.M.R. (DMSO-d$_6$,δ): 1.42 (9H, s), 1.67–2.69 (6H, m), 3.01 (2H, m), 3.73 (2H, m), 4.08–4.73 (4H, m), 5.18 (1H, d, J=5.0 Hz), 5.32 (1H, m), 5.69–6.32 (3H, m), 7.42 (1H, s), 8.55 (1H, s), 9.62 (1H, d, J=8.0 Hz)

(39) 7-[2-(2-Cyclohexen-1-yl)oxyimino-2-(2-formamidothiazol-4-yl)acetamido]-3-carbamoyloxymethyl-3-cephem-4-carboxylic acid (syn isomer).

I.R. (Nujol): 3260, 1780, 1680 (broad), 1540 cm$^{-1}$

N.M.R. (DMSO-d$_6$,δ): 1.3–2.3 (6H, m), 3.55 (2H, broad s), 4.50–5.10 (3H, m), 5.20 (1H, d, J=5 Hz), 5.67–6.17 (3H, m), 6.57 (2H, broad s), 7.38 (1H, s), 8.52 (1H, s), 9.60 (1H, d, J=8 Hz), 12.60 (1H, broad s)

(40) 7-[2-(2-Cyclohexen-1-yl)oxyimino-2-(2-formamidothiazol-4-yl)acetamido]-3-[1-(2-carboxyethyl)-1H-tetrazol-5-yl]thiomethyl-3-cephem-4-carboxylic acid (syn isomer).

I.R. (Nujol): 3180, 1770, 1660 cm$^{-1}$

N.M.R. (DMSO-d$_6$,δ): 1.28–2.30 (6H, m), 2.97 (2H, m), 3.75 (2H, m), 4.22–4.95 (5H, m), 5.17 (1H, d, J=5.0 Hz), 5.66–6.23 (3H, m), 7.43 (1H, s), 8.56 (1H, s), 9.66 (1H, d, J=8.0 Hz)

(41) 7-[2-(2-Cyclopenten-1-yl)oxyimino-2-(2-aminothiazol-4-yl)acetamido]-3-[1-(2-carboxyethyl)-1H-tetrazol-5-yl]thiomethyl-3-cephem-4-carboxylic acid (syn isomer).

I.R. (Nujol): 3270, 1765, 1660, 1630 cm$^{-1}$

(42) 7-[2-(2-Cyclopenten-1-yl)oxyimino-2-(2-aminothiazol-4-yl)acetamido]-3-(1H-1,2,3-triazol-5-yl)thiomethyl-3-cephem-4-carboxylic acid (syn isomer). mp. 175°–185° C. (dec.).

I.R. (Nujol): 3420, 3250, 1760, 1650, 1530 cm$^{-1}$

(43) 7-[2-(2-Cyclopenten-1-yl)oxyimino-2-(2-aminothiazol-4-yl)acetamido]-3-[1-(3-aminopropyl)-1H-tetrazol-5-yl]thiomethyl-3-cephem-4-carboxylic acid (syn isomer).

I.R. (Nujol): 3180, 1760, 1660, 1620 cm$^{-1}$

(44) 7-[2-(2-Cyclopenten-1-yl)oxyimino-2-(2-aminothiazol-4-yl)acetamido]-3-(tetrazolo[1,5-b]pyridazin-6-yl)thiomethyl-3-cephem-4-carboxylic acid (syn isomer). mp. 178° to 180° C. (dec.).

I.R. (Nujol): 3280, 3180, 1770, 1650, 1620 cm$^{-1}$

(45) 7-[2-(2-Cyclohexen-1-yl)oxyimino-2-(2-aminothiazol-4-yl)acetamido]-3-carbamoyloxymethyl-3-cephem-4-carboxylic acid (syn isomer). mp. 230° to 235° C. (dec.).

I.R. (Nujol): 3440, 3330, 3270, 1750, 1690, 1630, 1530 cm$^{-1}$

(46) 7-[2-(2-Cyclohexen-1-yl)oxyimino-2-(2-aminothiazol-4-yl)acetamido]-3-[1-(2-carboxyethyl)-1H-tetrazol-5-yl]thiomethyl-3-cephem-4-carboxylic acid (syn isomer).

I.R. (Nujol): 3300, 3200, 1770, 1660, 1630 cm$^{-1}$

(47) N-[7-[2-(2-Cyclopenten-1-yl)oxyimino-2-(2-aminothiazol-4-yl)acetamido]-3-cephem-3-ylmethyl]-3'-hydroxymethylpyridinium-4-carboxylate (syn isomer)

I.R. (Nujol): 3400–3150, 1770, 1660, 1610, 1530 cm$^{-}$

(48) N-[7-[2-(2-Cyclopenten-1-yl)oxyimino-2-(2-aminothiazol-4yl)acetamido]-3-cephem-3-ylmethyl]-3'-carbamoylpyridinium-4-carboxylate (syn isomer).

I.R. (Nujol): 3400–3200, 1780, 1680, 1615, 1530 cm$^{-}$

EXAMPLE 13

A mixture of 7-[2-(2-cyclopenten-1-yl)oxyimino-2-(2-formamidothiazol-4-yl)acetamido]-3-cephem-4-carboxylic acid (syn isomer) (1.6 g), conc.hydrochloric acid (1.1 g), methanol (20 ml) and tetrahydrofuran (15 ml) was stirred for 2 hours at room temperature. The reaction mixture was evaporated. The residue was dissolved in an aqueous solution of sodium bicarbonate and the solution was adjusted to pH 3.0 with hydrochloric acid. The precipitates were collected by filtration, washed with water and dried over phosphorus pentoxide to give 7-[2-(2-cyclopenten-1-yl)oxyimino-2-(2-aminothiazol-4-yl)acetamido]-3-cephem-4-carboxylic acid (syn isomer) (1.3 g). mp. 201° to 213° C. (dec.).

I.R. (Nujol): 3400–3100, 1770, 1650, 1620, 1540 cm$^{-1}$

N.M.R. (DMSO-d$_6$, δ) 1.56–2.68 (4H, m), 3.56 (2H, broad s), 5.08 (1H, d, J=5 Hz), 5.26 (1H, m), 5.44–5.98 (2H, m), 6.18 (1H, m), 6.46 (1H, m), 6.7 (1H, s), 9.50 (1H, d, J=8 Hz)

EXAMPLE 14

A mixture of 7-[2-(2-cyclopenten-1-yl)oxyimino-2-{2-(2,2,2-trifluoroacetamido)thiazol-4-yl}acetamido]cephalosporanic acid (syn isomer) (1.8 g), sodium acetate trihydrate (4.1 g), water (50 ml) and tetrahydrofuran (2 ml) was stirred for 20 hours at room temperature. After the addition of ethyl acetate, the aqueous layer was separated and evaporated. The residue was adjusted to pH 3.0 with 10% hydrochloric acid and the precipitates were collected by filtration, washed with water and then dried over phosphorus pentoxide to give 7-[2-(2-cyclopenten-1-yl)oxyimino-2-(2-aminothiazol-4-yl)acetamido]cephalosporanic acid (syn isomer) (1.1 g). mp. 141° to 150° C. (dec.).

I.R. (Nujol): 3400–3100, 1770, 1730, 1650, 1530 cm$^{-1}$

N.M.R. (DMSO-d$_6$, δ) 1.32–2.78 (4H, m), 3.58 (2H, broad s), 4.87 (2H, q, J=13 Hz), 5.17 (1H, d, J=5 Hz), 5.32 (1H, m), 6.3–5.6 (3H, m), 6.76 (1H, s), 9.58 (1H, d, J=8 Hz)

EXAMPLE 15

A mixture of 7-[2-(2-cyclopenten-1-yl)oxyimino-2-(2-formamidothiazol-4-yl)acetamido]-3-(1,3,4-thiadiazol-2-yl)thiomethyl-3-cephem-4-carboxylic acid (syn isomer) (2.5 g), methanol (17.5 ml), conc.hydrochloric acid (0.88 g) and tetrahydrofuran (5.0 ml) was stirred for 1.5 hours at room temperature. To the reaction mixture were added water and a saturated aqueous solution of sodium bicarbonate so that the pH was adjusted to pH 5.0. The resulting mixture was evaporated and to the residue was added ethyl acetate. The mixture was adjusted to pH 7.5 with a saturated aqueous solution of sodium bicarbonate. The aqueous layer was separated, washed with ethyl acetate and evaporated and then the residue was adjusted to pH 3.0 with 10% hydrochloric acid. The precipitates were collected by filtration, washed with water, dried over phosphorus pentoxide under reduced pressure to give 7-[2-(2-cyclopenten-1-yl)oxyimino-2-(2-aminothiazol-4-yl)acetamido]-3-

(1,3,4-thiadiazol-2-yl)thiomethyl-3-cephem-4-carboxylic acid (syn isomer) (2.00 g). mp. 152° to 157° C. (dec.).
I.R. (Nujol): 3340, 1775, 1655 cm$^{-1}$
N.M.R. (DMSO-d$_6$, δ) 1.66–2.81 (4H, m), 3.71 (2H, m), 4.47 (2H, q, J=14 Hz), 4.99–5.57 (2H, m), 5.57–6.38 (3H, m), 6.76 (1H, s), 9.55 (1H, d, J=8.0 Hz), 9.59 (1H, s)

EXAMPLE 16

A mixture of 7-[2-(2-cyclopenten-1-yl)oxyimino-2-(2-formamidothiazol-4-yl)acetamido]-3-(5-tert-butoxycarboxamidomethyl-1,3,4-thiadiazol-2-yl)thiomethyl-3-cephem-4-carboxylic acid (syn isomer) (2.3 g), conc.hydrochloric acid (1.35 g) and methanol (30 ml) was stirred for 2 hours at room temperature. The reaction mixture was evaporated. The residue was dissolved in an aqueous solution of sodium bicarbonate and insoluble materials were filtered out. The filtrate was adjusted to pH 3.5 with 10% hydrochloric acid and then subjected to column chromatography (Non-ion adsorption resin, Diaion HP20 prepared by Mitsubishi Chemical Industries) using 40% isopropyl alcohol as an eluent to give 7-[2-(2-cyclopenten-1-yl)oxyimino-2-(2-aminothiazol-4-yl)acetamido]-3-(5-aminomethyl-1,3,4-thiadiazol-2-yl)thiomethyl-3-cephem-4-carboxylic acid (syn isomer) (0.48 g). mp. 145° to 170° C. (dec.).
I.R. (Nujol): 3150, 1760, 1650, 1610, 1520 cm$^{-1}$
N.M.R. (DMSO-d$_6$, δ) 1.87–2.57 (4H, m), 3.60 (2H, m), 4.3–4.03 (2H, m), 4.47 (2H, broad s), 5.0–5.27 (2H, m), 5.53–6.63 (3H, m), 6.63 (1H, s), 9.43 (1H, d, J=8 Hz)

EXAMPLE 17

A suspension of 7-[2-(2-cyclopenten-1-yl)oxyimino-2-(2-formamidothiazol-4-yl)acetamido]-3-(tetrazolo[1,5-b]pyridazin-6-yl)thiomethyl-3-cephem-4-carboxylic acid (syn isomer) (1.7 g) in methanol (12.0 ml) and conc.hydrochloric acid (0.56 g) was stirred and then thereto was added tetrahydrofuran (12.0 ml) to give a homogenous solution, which was stirred for 2 hours and 50 minutes at room temperature. To the reaction mixture were added water and sodium bicarbonate so that the pH was adjusted to 5.0. After the concentration of the mixture, to the concentrate were added ethyl acetate, water and sodium bicarbonate so that the pH was adjusted to 7.5. The aqueous layer was separated, washed with ethyl acetate (×2), concentrated and adjusted to pH 3.0 with 10% hydrochloric acid. The precipitates were collected by filtration, washed with water, dried over phosphorus pentoxide under reduced pressure to give 7-[2-(2-cyclopenten-1-yl)oxyimino-2-(2-aminothiazol-4-yl)acetamido]-3-(tetrazolo[1,5-b]pyridazin-6-yl)thiomethyl-3-cephem-4-carboxylic acid (syn isomer) (1.00 g). mp. 178° to 180° C. (dec.).
I.R. (Nujol): 3280, 3180, 1770, 1650, 1620 cm$^{-1}$
N.M.R. (DMSO-d$_6$, δ): 1.66–2.72 (4H, m), 3.71 (2H, m), 4.42 (2H, ABq, J=13.0 Hz), 4.98–5.42 (2H, m), 5.62–6.23 (3H, m), 6.67 (1H, s), 7.69 (1H, d, J=10.0 Hz), 8.52 (1H, d, J=10.0 Hz), 9.44 (1H, d, J=8.0 Hz)

EXAMPLE 18

A mixture of 7-[2-(2-cyclopenten-1-yl)oxyimino-2-{2-(2,2,2-trifluoroacetamidothiazol-4-yl}acetamido]-3-(1H-1,2,3-triazol-5-yl)thiomethyl-3-cephem-4-carboxylic acid (syn isomer) (1.4 g), sodium acetate (1.78 g) and water (60 ml) was stirred over night at room temperature. The aqueous layer was separated from the reaction mixture, adjusted to pH 3.0 with 10% hydrochloric acid. The precipitates were collected by filtration, washed with water to give 7-[2-(2-cyclopenten-1-yl)oxyimino-2-(2-aminothiazol-4-yl)acetamido]-3-(1H-1,2,3-triazol-5-yl)thiomethyl-3-cephem-4-carboxylic acid (syn isomer) (0.8 g) mp. 175° to 185° C. (dec.).
I.R. (Nujol): 3420, 3250, 1760, 1650, 1530 cm$^{-1}$
N.M.R. (DMSO-d$_6$, δ): 1.63–2.50 (4H, m), 3.60 (2H, m), 3.93 (2H, m), 5.07 (1H, d, J=5 Hz), 5.13–5.43 (1H, m), 5.50–6.23 (2H, m), 6.67 (1H, s), 7.90 (1H, s), 9.52 (1H, d, J=8 Hz)

EXAMPLE 19

The following compounds were prepared according to a similar manner to those of Examples 13 to 18.

(1) 7-[2-(2-Cyclopenten-1-yl)oxyimino-2-(2-aminothiazol-4-yl)acetamido]-2-methyl-3-cephem-4-carboxylic acid (syn isomer).
I.R. (Nujol): 3300, 1770, 1660, 1630 cm$^{-1}$
N.M.R. (DMSO-d$_6$, δ) 1.42 (3H, d, J=7 Hz), 1.74–2.7 (4H, m), 3.57–4.04 (1H, m), 5.12 (1H, d, J=5 Hz), 5.14–5.64 (1H, m), 5.85 (1H, dd, J=5 and 8 Hz), 5.87–6.24 (2H, m), 6.55 (1H, d, J=6 Hz), 6.7 (1H, s), 7.24 (2H, broad s), 9.50 (1H, d, J=8 Hz)

(2) 7-[2-(2-Cyclopenten-1-yl)oxyimino-2-(2-aminothiazol-4-yl)acetamido]-3-carbamoyloxymethyl-3-cephem-4-carboxylic acid (syn isomer). mp. 182° to 195° C. (dec.).
I.R. (Nujol): 3250, 1760, 1700, 1650, 1540 cm$^{-1}$
N.M.R. (DMSO-d$_6$, δ) 1.78–2.53 (4H, m), 3.53 (2H, broad s), 4.78 (2H, q, J=13 Hz), 5.17 (1H, d, J=5 Hz), 5.30 (1H, m), 5.60–6.33 (3H, s), 6.60 (2H, broad s), 6.77 (1H, s), 9.57 (1H, d, J=8 Hz)

(3) Benzhydryl 7-[2-(2-cyclopenten-1-yl)oxyimino-2-(2-aminothiazol-4-yl)acetamido]-3-(2-tertbutoxycarboxamidoethyl)thiomethyl-3-cephem-4-carboxylate (syn isomer)
I.R. (Nujol): 3500–3200, 1780, 1680, 1620, 1530 cm$^{-1}$
N.M.R. (DMSO-d$_6$, δ) 1.33 (9H, s), 1.90–2.50 (4H, m), 2.93 (2H, m), 3.43–3.77 (4H, m), 5.20 (1H, d, J=5 Hz), 5.27 (1H, m), 5.60–6.17 (5H, m), 6.70 (1H, s), 6.88 (1H, s), 7.00–7.67 (10H, m), 9.52 (1H, d, J=8 Hz)

(4) 7-[2-(2-Cyclopenten-1-yl)oxyimino-2-(2-aminothiazol-4-yl)acetamido]-3-(2-aminoethyl)thiomethyl-3-cephem-4-carboxylic acid (syn isomer)
I.R. (Nujol): 3350–3100, 1760, 1660, 1610, 1515 cm$^{-1}$ (5) 7-[2-(2-Cyclopenten-1-yl)oxyimino-2-(2-aminothiazol-4-yl)acetamido]-3-(5-methyl-1,3,4-thiadiazol-2-yl)thiomethyl-3-cephem-4-carboxylic acid (syn isomer). mp. 148° to 152° C.
I.R. (Nujol): 3260, 1870, 1650 cm$^{-1}$
N.M.R. (DMSO-d$_6$, δ) 1.5–2.87 (4H, m), 2.87 (3H, s), 3.68 (2H, m), 4.40 (2H, dd, J=15 and 21 Hz), 5.13 (1H, d, J=5 Hz), 5.1–5.5 (1H, m), 5.77 (1H, dd, J=5 and 8 Hz), 5.83–6.29 (2H, m), 6.72 (1H, s), 7.2 (2H, m), 9.5 (1H, d, J=8 Hz)

(6) 7-[2-(2-Cyclopenten-1-yl)oxyimino-2-(2-aminothiazol-4-yl)acetamido]-3-(1-methyl-1H-tetrazol-5-yl)thiomethyl-3-cephem-4-carboxylic acid (syn isomer). mp. 147° to 150° C.
I.R. (Nujol): 3300, 1770, 1660 cm$^{-1}$
N.M.R. (DMSO-d$_6$, δ) 1.67–2.69 (4H, m), 3.68 (2H, m), 3.93 (3H, s), 4.32 (2H, m), 5.12 (1H, d, J=5 Hz), 5.1–5.43 (1H, m), 5.78 (1H, dd, J=5 and 8 Hz), 5.9–6.32 (2H, m), 6.7 (1H, s), 7.2 (2H, m), 9.5 (1H, d, J=8 Hz)

(7) 7-[2-(2-Cyclopenten-1-yl)oxyimino-2-(2-aminothiazol-4-yl)acetamido]-3-(1-allyl-1H-tetrazol-5-yl)thiomethyl-3-cephem-4-carboxylic acid (syn isomer). mp. 145° to 153° C. (dec.).
I.R. (Nujol): 3400–3100, 1770, 1670, 1620, 1520 cm$^{-1}$ N.M.R. (DMSO-d$_6$, δ) 1.52–2.8 (4H, m), 3.7 (2H, broad s), 4.37 (2H, q, J=13 Hz), 4.83–5.48 (6H, m) 5.63–6.53 (4H, m), 6.72 (1H, s), 9.48 (1H, d, J=8 Hz)

(8) 7-[2-(2-Cyclopenten-1-yl)oxyimino-2-(2-aminothiazol-4-yl)acetamido]-3-(1-carboxymethyl-1H-tetrazol-5-yl)thiomethyl-3-cephem-4-carboxylic acid (syn isomer). mp. 164° to 170° C. (dec.).

I.R. (Nujol): 3280, 1765, 1655 cm$^{-1}$

N.M.R. (DMSO-d$_6$, δ) 1.76–2.79 (4H, m), 3.70 (2H, m), 4.39 (2H, q, J=14.0 Hz), 5.13 (1H, d, J=5.0 Hz), 5.03–5.56 (3H, m), 5.65–6.35 (3H, m), 6.74 (1H, s), 9.56 (1H, d, J=7.0 Hz)

(9) 7-[2-(2-Cyclopenten-1-yl)oxyimino-2-(2-aminothiazol-4-yl)acetamido]-3-(4-carboxypyridin-2-yl)thiomethyl-3-cephem-4-carboxylic acid (syn isomer). mp. 174° to 205° C. (dec.).

I.R. (Nujol): 1760, 1670, 1620, 1450, 1370, 1360 cm$^{-1}$

N.M.R. (DMSO-d$_6$, δ) 1.77–2.50 (4H, m), 3.50–3.77 (2H, m), 4.30 (2H, ABq, J=15 Hz), 5.10–5.43 (2H, m), 5.57–6.37 (3H, m), 6.73 (1H, s), 7.50–7.77 (2H, m), 8.60–8.67 (1H, m), 9.53 (1H, d, J=8 Hz)

(10) 7-[2-(2-Cyclopenten-1-yl)oxyimino-2-(2-aminothiazol-4-yl)acetamido]-3-(1H-tetrazol-5-yl)thiomethyl-3-cephem-4-carboxylic acid (syn isomer). mp. 165° to 172° C. (dec.).

I.R. (Nujol): 3300, 1770, 1660, 1630 cm$^{-1}$

N.M.R. (DMSO-d$_6$, δ) 1.56–2.68 (4H, m), 3.70 (2H, m), 4.34 (2H, q, J=13.0 Hz), 5.03–5.54 (2H, m), 5.61–6.30 (3H, m), 6.76 (1H, s), 9.56 (1H, d, J=8.0 Hz)

(11) 7-[2-(2-Cyclohexen-1-yl)oxyimino-2-(2-aminothiazol-4-yl)acetamido]-3-cephem-4-carboxylic acid (syn isomer). mp. 220° to 241° C. (dec.).

I.R. (Nujol): 3400–3100, 1770, 1650, 1630, 1530 cm$^{-1}$

N.M.R. (DMSO-d$_6$, δ) 1.37–2.4 (6H, m), 3.65 (2H, m), 4.67 (1H, m), 5.13 (1H, d, J=5 Hz), 5.62–6.31 (3H, m), 6.53 (1H, m), 6.75 (1H, s), 9.56 (1H, d, J=8 Hz)

(12) 7-[2-(2-Cyclohexen-1-yl)oxyimino-2-(2-aminothiazol-4-yl)acetamido]-2-methyl-3-cephem-4-carboxylic acid (syn isomer). mp. 159° to 166° C. (dec.).

I.R. (Nujol): 3400–3100, 1770, 1660, 1630, 1520 cm$^{-1}$

N.M.R. (DMSO-d$_6$, δ) 1.47 (3H, d, J=7 Hz), 1.08–2.3 (6H, m), 4.18–3.48 (1H, m), 5.13 (1H, d, J=5 Hz), 4.67 (1H, m) 5.5–6.25 (3H, m), 6.77 (1H, s), 9.57 (1H, d, J=8 Hz)

(13) 7-[2-(2-Cyclohexen-1-yl)oxyimino-2-(2-aminothiazol-4-yl)acetamido]-3-(1,3,4-thiadiazol-2yl)thiomethyl-3-cephem-4-carboxylic acid (syn isomer).

I.R. (Nujol): 3400–3100, 1770, 1660, 1620, 1530 cm$^{-1}$

N.M.R. (DMSO-d$_6$, δ) 1.07–2.25 (6H, m), 3.7 (2H, broad s), 4.45 (2H, q, J=12 Hz), 4.23–4.92 (1H, m), 5.15 (1H, d, J=5 Hz), 5.87–6.17 (3H, m), 6.77 (1H, s), 9.58 (1H, d, J=8 Hz), 9.58 (1H, s)

(14) 7-[2-(2-Cyclohexen-1-yl)oxyimino-2-(2-aminothiazol-4-yl)acetamido]-3-(1-methyl-1H-tetrazol-5-yl)thiomethyl-3-cephem-4-carboxylic acid (syn isomer). mp. 156° to 160° C. (dec.).

I.R. (Nujol): 3400–3100, 1770, 1660, 1620, 1520 cm$^{-1}$

N.M.R. (DMSO-d$_6$, δ) 1.18–2.22 (6H, m), 3.67 (2H, broad s), 3.93 (3H, s), 4.3 (2H, m), 4.57 (1H, m), 5.12 (1H, d, J=5 Hz), 5.35–6.17 (3H, m), 6.73 (1H, s), 9.58 (1H, d, J=8 Hz)

(15) 7-[2-(2-Cyclohexen-1-yl)oxyimino-2-(2-aminothiazol-4-yl)acetamido]-3-(1-allyl-1H-tetrazol-5-yl)thiomethyl-3-cephem-4-carboxylic acid (syn isomer). mp. 148° to 157° C. (dec.).

I.R. (Nujol): 3400–3100, 1770, 1670, 1620, 1520 cm$^{-1}$

N.M.R. (DMSO-d$_6$, δ) 1.05–2.38 (6H, m), 3.68 (2H, broad s), 4.38 (2H, m), 4.65 (1H, m), 4.8–5.53 (5H, m), 5.6–6.42 (4H, m), 6.73 (1H, s), 9.53 (1H, d, J=8 Hz)

(16) 7-[2-(2-Cyclohexen-1-yl)oxyimino-2-(2-aminothiazol-4-yl)acetamido]-3-(1-carboxymethyl-1H-tetrazol-5-yl)thiomethyl-3-cephem-4-carboxylic acid (syn isomer). mp. 166° to 182° C. (dec.).

I.R. (Nujol): 3400–3100, 1770, 1660, 1620, 1530 cm$^{-1}$

N.M.R. (DMSO-d$_6$, δ) 1.1–2.25 (6H, m), 3.68 (2H, m), 4.37 (2H, m), 4.63 (1H, m), 5.12 (1H, d, J=5 Hz), 5.3 (2H, s), 5.07 (3H, m), 6.7 (1H, s), 9.52 (1H, d, J=8 Hz)

(17) 7-[2-(2-Cyclohexen-1-yl)oxyimino-2-(2-aminothiazol-4-yl)acetamido]-3-(1H-tetrazol-5-yl)thiomethyl-3-cephem-4-carboxylic acid (syn isomer).

I.R. (Nujol): 3400–3100, 1770, 1660, 1630, 1520 cm$^{-1}$

N.M.R. (DMSO-d$_6$, δ) 1.17–2.32 (6H, m), 3.68 (2H, broad s), 4.33 (2H, m), 4.6 (1H, m), 5.12 (1H, d, J=5 Hz), 6.13–5.57 (3H, m), 6.73 (1H, s), 9.52 (1H, d, J=8 Hz)

(18) 7-[2-(2-Cyclopenten-1-yl)oxyimino-2-(2-aminothiazol-4-yl)acetamido]-3-[1-(2-hydroxyethyl)-1H-tetrazol-5-yl]thiomethyl-3-cephem-4-carboxylic acid (syn isomer). mp 162° to 168° C. (dec.).

I.R. (Nujol): 3400–3100, 1770, 1720, 1650, 1540 cm$^{-1}$

N.M.R. (DMSO-d$_6$) 1.45–2.68 (4H, m), 3.53–4.00 (2H, m), 4.08–4.67 (4H, m), 5.15 (1H, d, J=5 Hz), 5.35 (1H, m), 5.65–6.3 (3H, m), 6.87 (1H, s), 9.67 (1H, d, J=8 Hz)

(19) 7-[2-(2-Cyclohexen-1-yl)oxyimino-2-(2-aminothiazol-4-yl)acetamido]cephalosporanic acid (syn isomer).

I.R. (Nujol): 3400–3100, 1770, 1740, 1660, 1630, 1520 cm$^{-1}$

(20) 7-[2-(2-Cyclopenten-1-yl)oxyimino-2-(2-aminothiazol-4-yl)acetamido]-3-[1-(2-carboxyethyl)-1H-tetrazol-5-yl]thiomethyl-3-cephem-4-carboxylic acid (syn isomer).

I.R. (Nujol): 3270, 1765, 1660, 1630 cm$^{-1}$

N.M.R. (DMSO-d$_6$, δ): 1.67–1.73 (4H, m), 2.90 (2H, t, J=6.0 Hz), 3.67 (2H, m), 4.01–4.70 (4H, m), 5.06 (1H, d, J=5.0 Hz), 5.20 (1H, m), 5.50–6.18 (3H, m), 6.63 (1H, s), 9.40 (1H, d, J=8.0 Hz)

(21) 7-[2-(2-Cyclopenten-1-yl)oxyimino-2-(2-aminothiazol-4-yl)acetamido]-3-[1-(3-aminopropyl)-1H-tetrazol-5-yl]thiomethyl-3-cephem-4-carboxylic acid (syn isomer).

I.R. (Nujol): 3180, 1760, 1660, 1620 cm$^{-1}$

N.M.R. (DMSO-d$_6$, δ): 1.68–2.60 (4H, m), 2.96 (2H, m), 3.51 (2H, m), 4.06–4.67 (4H, m), 5.01 (1H, d, J=5 Hz), 5.26 (1H, m), 5.47–6.28 (3H, m), 6.70 (1H, s), 9.45 (1H, d, J=8 Hz).

(22) 7-[2-(2-Cyclohexen-1-yl)oxyimino-2-(2-aminothiazol-4-yl)acetamido]-3-carbamoyloxymethyl-3-cephem-4-carboxylic acid (syn isomer). mp. 230° to 235° C. (dec.).

I.R. (Nujol): 3440, 3330, 3270, 1750, 1690, 1630, 1530 cm$^{-1}$

N.M.R. (DMSO-d$_6$, δ): 1.13–2.27 (6H, m), 3.50 (2H, broad s), 4.43–4.93 (3H, m), 5.15 (1H, d, J=5 Hz), 5.57–6.07 (3H, m), 6.57 (1H, broad s), 6.70 (1H, s), 9.53 (1H, d, J=8 Hz)

(23) 7-[2-(2-Cyclohexen-1-yl)oxyimino-2-(2-aminothiazol-4-yl)acetamido]-3-[1-(2-carboxyethyl)-1H-tetrazol-5-yl]thiomethyl-3-cephem-4-carboxylic acid (syn isomer)

I.R. (Nujol): 3300, 3200, 1770, 1660, 1630 cm$^{-1}$

N.M.R. (DMSO-d$_6$, δ): 1.30–2.26 (6H, m), 2.95 (2H, t, J=6.0 Hz), 3.72 (2H, m), 4.08–4.84 (5H, m), 5.13 (1H, d, J=4.0 Hz), 5.61–6.11 (3H, m), 6.73 (1H, s), 9.54 (1H, d, J=8.0 Hz).

(24) N-[7-{2-(2-Cyclopenten-1-yl)oxyimino-2-(2-aminothiazol-4-yl)acetamido}-3-cephem-3-ylmethyl]-pyridinium-4-carboxylate (syn isomer).

mp. 171° to 180° C. (dec.).

I.R. (Nujol): 3400–3100, 1770, 1660, 1610, 1530 cm$^{-1}$

(25) N-[7-[2-(2-Cyclopenten-1-yl)oxyimino-2-(2-aminothiazol-4-yl)acetamido]-3-cephem-3-ylmethyl]-3'-hydroxymethylpyridinium-4-carboxylate (syn isomer)

I.R. (Nujol): 3400–3150, 1770, 1660, 1610, 1530 cm$^-$

(26) N-[7-[2-(2-Cyclopenten-1-yl)oxyimino-2-(2-aminothiazol-4-yl)acetamido]-3-cephem-3-ylmethyl]-3'-carbamoylpyridinium-4-carboxylate (syn isomer).

I.R. (Nujol): 3400–3200, 1780, 1680, 1615, 1530 cm$^-$

EXAMPLE 20

To a solution of 7-[2-(2-cyclopenten-1-yl)oxyimino-2-(2-aminothiazol-4-yl)acetamido]cephalosporanic acid (syn isomer) (1.52 g) in phosphate buffer (pH 6.4) (150 ml) was added 1,3,4-thiadiazole-2-thiol (0.53 g) and the mixture was stirred for 3 hours at 55° to 60° C. The reaction mixture was cooled and adjusted to pH 3 with 10% hydrochloric acid. The precipitates were collected by filtration, washed with water and then dried to give 7-[2-(2-cyclopenten-1-yl)oxyimino-2-(2-aminothiazol-4-yl)acetamido]-3-(1,3,4-thiadiazol-2-yl)thiomethyl-3-cephem-4-carboxylic acid (syn isomer) (0.73 g).

I.R. (Nujol): 3340, 1775, 1655 cm$^{-1}$

EXAMPLE 21

Pyridine (1.2 g) was added to a solution of 7-[2-(2-cyclopenten-1-yl)oxyimino-2-(2-aminothiazol-4-yl)acetamido]cephalosporanic acid (syn isomer) (3.0 g) and sodium bicarbonate (0.5 g) in water (30 ml) at 50° C. After the addition of sodium iodide (9 g) at 80° C., the mixture was stirred for 40 minutes at the same temperature. The reaction mixture was cooled to 5° C., adjusted to pH 2.0 with 10% hydrochloric acid and then filtered. The filtrate was subjected to column chromatography (non-ion) adsorption resin, Diaion HP20 prepared by Mitsubishi Chemical Industries) and eluted with 30% aqueous solution of methanol. The fractions containing the object compound were combined, concentrated and then lyophilized to give N-[7-{2-(2-cyclopenten-1-yl)oxyimino-2-(2-aminothiazol-4-yl)acetamido}-3-cephem-3-ylmethyl]pyridinium-4-carboxylate (syn isomer) (0.35 g). This product was identified with the authentic sample.

EXAMPLE 22

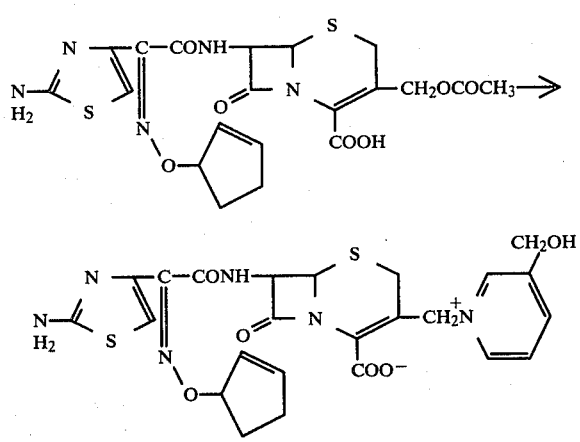

A mixture of 7-[2-(2-cyclopenten-1-yl)oxyimino-2-(2-aminothiazol-4-yl)acetamido]cephalosporanic acid (syn isomer) (4.92 g), sodium bicarbonate (0.84 g), 3-hydroxymethylpyridine (5.5 g) and sodium iodide (21 g) in water (6 ml) was stirred for an hour at 80° to 81° C. The reaction mixture was dissolved in water (300 ml) and washed with ethyl acetate. The aqueous layer was separated, adjusted to PH 1.0 with 10% aqueous hydrochloric acid and the precipitates were filtered off. The filtrate was adjusted to PH 5.5 with 10% aqueous solution of sodium hydroxide. After removing the solvent under reduced pressure, the aqueous solution was adjusted to PH 3.6 with aqueous hydrochloric acid under ice cooling. The solution was subjected to column chromatography on macroporous non-ionic adsorption resin "Diaion HP-20" (Trademark: Mitsubishi Chemical Industries) and eluted with 40% aqueous solution of isopropyl alcohol. The fractions containing the object compound were concentrated in vacuo and lyophylized to give N-[7-[2-(2-cyclopenten-1-yl)oxyimino-2-(2-aminothiazol-4-yl)acetamido]-3-cephem-3-yl-methyl]-3'-hydroxymethylpyridinium-4-carboxylate (syn isomer) (0.7 g).

I.R. (Nujol): 3400–3150, 1770, 1660, 1610, 1530 cm$^-$

N.M.R. (D$_2$O+DCL, δ): 1.5–3.00 (4H, m), 3.7 (2H, m), 5.27–6.5 (7H, m), 5.40 (1H, d, J=5 Hz), 6.00 (1H, d, J=5 Hz), 7.22 (1H, s), 8.25 (1H, m) 8.5–9.17 (3H, m)

EXAMPLE 23

The following compounds were prepared according to a similar manner to that of Examples 20 to 22.

(1) Benzhydryl 7-[2-(2-cyclopenten-1-yl)oxyimino-2-(2-aminothiazol-4-yl)acetamido]-3-(2-tert-butoxycarboxamidoethyl)thiomethyl-3-cephem-4-carboxylate (syn isomer).

I.R. (Nujol): 3500–3200, 1780, 1680, 1620, 1530 cm$^{-1}$ (2) 7-[2-(2-Cyclopenten-1-yl)oxyimino-2-(2-aminothiazol-4-yl)acetamido]-3-(2-aminoethyl)thiomethyl-3-cephem-4-carboxylic acid (syn isomer).

I.R. (Nujol): 3350–3100, 1760, 1660, 1610, 1515 cm$^{-1}$ (3) 7-[2-(2-Cyclopenten-1-yl)oxyimino-2-(2-aminothiazol-4-yl)acetamido]-3-(5-methyl-1,3,4-thiadiazol-2-yl)thiomethyl-3-cephem-4-carboxylic acid (syn isomer). mp. 148° to 152° C.

I.R. (Nujol): 3260, 1770, 1650 cm$^{-1}$ (4) 7-[2-(2-Cyclopenten-1-yl)oxyimino-2-(2-aminothiazol-4-yl)acetamido]-3-(1-methyl-1H-tetrazol-5-yl)thiomethyl-3-cephem-4-carboxylic acid (syn isomer). mp. 147° to 150° C.

I.R. (Nujol): 3300, 1770, 1660 cm$^{-1}$ (5) 7-[2-(2-Cyclopenten-1-yl)oxyimino-2-(2-aminothiazol-4-yl)acetamido]-3-(1-allyl-1H-tetrazol-5-yl)thiomethyl-3-cephem-4-carboxylic acid (syn isomer). mp. 145° to 153° C. (dec.).

I.R. (Nujol): 3400–3100, 1770, 1670, 1620, 1520 cm$^{-1}$ (6) 7-[2-(2-Cyclopenten-1-yl)oxyimino-2-(2-aminothiazol-4-yl)acetamido]-3-(1-carboxymethyl-1H-tetrazol-5-yl)thiomethyl-3-cephem-4-carboxylic acid (syn isomer). mp. 164° to 170° C. (dec.).

I.R. (Nujol): 3280, 1765, 1655 cm$^{-1}$ (7) 7-[2-(2-Cyclopenten-1-yl)oxyimino-2-(2-aminothiazol-4-yl)acetamido]-3-(4-carboxypyridin-2-yl)thiomethyl-3-cephem-4-carboxylic acid (syn isomer). mp. 174° to 205° C. (dec.).

I.R. (Nujol): 1760, 1670, 1620, 1450, 1370, 1360 cm$^{-1}$ (8) 7-[2-(2-Cyclopenten-1-yl)oxyimino-2-(2-aminothiazol-4-yl)acetamido]-3-(1H-tetrazol-5-yl)thiomethyl-3-cephem-4-carboxylic acid (syn isomer). mp. 165° to 172° C. (dec.).

I.R. (Nujol): 3300, 1770, 1660, 1630 cm$^{-1}$ (9) 7-[2-(2-Cyclopenten-1-yl)oxyimino-2-(2-aminothiazol-4-yl)acetamido]-3-(5-aminomethyl-1,3,4-thiadiazol-2-yl)thiomethyl-3-cephem-4-carboxylic acid (syn isomer). mp. 145° to 170° C. (dec.).
I.R. (Nujol): 3150, 1760, 1650, 1610, 1520 cm$^{-1}$

(10) 7-[2-(2-Cyclohexen-1-yl)oxyimino-2-(2-aminothiazol-4-yl)acetamido]-3-(1,3,4-thiadiazol-2-yl)thiomethyl-3-cephem-4-carboxylic acid (syn isomer).
I.R. (Nujol): 3400–3100, 1770, 1660, 1620, 1530 cm$^{-1}$

(11) 7-[2-(2-Cyclohexen-1-yl)oxyimino-2-(2-aminothiazol-4-yl)acetamido]-3-(1-methyl-1H-tetrazol-5-yl)thiomethyl-3-cephem-4-carboxylic acid (syn isomer). mp. 156° to 160° C. (dec.).
I.R. (Nujol): 3400–3100, 1770, 1660, 1620, 1520 cm$^{-1}$

(12) 7-[2-(2-Cyclohexen-1-yl)oxyimino-2-(2-aminothiazol-4-yl)acetamido]-3-(1-allyl-1H-tetrazol-5-yl)thiomethyl-3-cephem-4-carboxylic acid (syn isomer). mp. 148° to 157° C. (dec.).
I.R. (Nujol): 3400–3100, 1770, 1670, 1620, 1520 cm$^{-1}$

(13) 7-[2-(2-Cyclohexen-1-yl)oxyimino-2-(2-aminothiazol-4-yl)acetamido]-3-(1-carboxymethyl-1H-tetrazol-5-yl)thiomethyl-3-cephem-4-carboxylic acid (syn isomer). mp. 166° to 182° C. (dec.).
I.R. (Nujol): 3400–3100, 1770, 1660, 1620, 1530 cm$^{-1}$

(14) 7-[2-(2-Cyclohexen-1-yl)oxyimino-2-(2-aminothiazol-4-yl)acetamido]-3-(1H-tetrazol-5-yl)thiomethyl-3-cephem-4-carboxylic acid (syn isomer).
I.R. (Nujol): 3400–3100, 1770, 1660, 1630, 1520 cm$^{-1}$

(15) Benzhydryl 7-[2-(2-cyclopenten-1-yl)oxyimino-2-(2-formamidothiazol-4-yl)acetamido]-3-(2-tert-butoxycarboxamidoethyl)thiomethyl-3-cephem-4-carboxylate (syn isomer).
I.R. (Nujol): 3270, 3150, 1780, 1710, 1680, 1660, 1570, 1225 cm$^{-1}$

(16) 7-[2-(2-Cyclopenten-1-yl)oxyimino-2-(2-formamidothiazol-4-yl)acetamido]-3-(1,3,4-thiadiazol-2-yl)thiomethyl-3-cephem-4-carboxylic acid (syn isomer).
I.R. (Nujol): 3150, 1770, 1670 cm$^{-1}$

(17) 7-[2-(2-Cyclopenten-1-yl)oxyimino-2-(2-formamidothiazol-4-yl)acetamido]-3-(5-methyl-1,3,4-thiadiazol-2-yl)thiomethyl-3-cephem-4-carboxylic acid (syn isomer).
I.R. (Nujol): 3240, 1765, 1660 cm$^{-1}$

(18) 7-[2-(2-Cyclopenten-1-yl)oxyimino-2-(2-formamidothiazol-4-yl)acetamido]-3-(1-methyl-1H-tetrazol-5-yl)thiomethyl-3-cephem-4-carboxylic acid (syn isomer).
I.R. (Nujol): 3240, 1760, 1670 cm$^{-1}$

(19) 7-[2-(2-Cyclopenten-1-yl)oxyimino-2-(2-formamidothiazol-4-yl)acetamido]-3-(1-allyl-1H-tetrazol-5-yl)thiomethyl-3-cephem-4-carboxylic acid (syn isomer). mp. 120° to 139° C. (dec.).
I.R. (Nujol): 3400–3100, 1770, 1670, 1540 cm$^{-1}$

(20) 7-[2-(2-Cyclopenten-1-yl)oxyimino-2-(2-formamidothiazol-4-yl)acetamido]-3-(1-carboxymethyl-1H-tetrazol-5-yl)thiomethyl-3-cephem-4-carboxylic acid (syn isomer).
I.R. (Nujol): 3150, 1770, 1660 cm$^{-1}$

(21) 7-[2-(2-Cyclopenten-1-yl)oxyimino-2-(2-formamidothiazol-4-yl)acetamido]-3-(4-carboxypyridin-2-yl)thiomethyl-3-cephem-4-carboxylic acid (syn isomer).
I.R. (Nujol): 1770, 1690–1650, 1540 cm$^{-1}$

(22) 7-[2-(2-Cyclopenten-1-yl)oxyimino-2-(2-formamidothiazol-4-yl)acetamido]-3-(1H-tetrazol-5-yl)thiomethyl-3-cephem-4-carboxylic acid (syn isomer).
I.R. (Nujol): 1770, 1660 cm$^{-1}$

(23) 7-[2-(2-Cyclopenten-1-yl)oxyimino-2-(2-formamidothiazol-4-yl)acetamido]-3-(5-tert-butoxycarboxamidomethyl-1,3,4-thiadiazol-2-yl)thiomethyl-3-cephem-4-carboxylic acid (syn isomer).
I.R. (Nujol): 3270, 1780, 1700, 1680, 1530 cm$^{-1}$

(24) 7-[2-(2-Cyclohexen-1-yl)oxyimino-2-(2-formamidothiazol-4-yl)acetamido]-3-(1,3,4-thiadiazol-2-yl)thiomethyl-3-cephem-4-carboxylic acid (syn isomer).
I.R. (Nujol): 3300–3100, 1780, 1670, 1540 cm$^{-1}$

(25) 7-[2-(2-Cyclohexen-1-yl)oxyimino-2-(2-formamidothiazol-4-yl)acetamido]-3-(1-methyl-1H-tetrazol-5-yl)thiomethyl-3-cephem-4-carboxylic acid (syn isomer).
I.R. (Nujol): 3400–3100, 1780, 1660, 1550 cm$^{-1}$

(26) 7-[2-(2-Cyclohexen-1-yl)oxyimino-2-(2-formamidothiazol-4-yl)acetamido]-3-(1-allyl-1H-tetrazol-5-yl)thiomethyl-3-cephem-4-carboxylic acid (syn isomer).
I.R. (Nujol): 3400–3100, 1770, 1670, 1540 cm$^{-1}$

(27) 7-[2-(2-Cyclohexen-1-yl)oxyimino-2-(2-formamidothiazol-4-yl)acetamido]-3-(1-carboxymethyl-1H-tetrazol-5-yl)thiomethyl-3-cephem-4-carboxylic acid (syn isomer).
I.R. (Nujol): 3400–3100, 1770, 1670, 1540 cm$^{-1}$

(28) 7-[2-(2-Cyclohexen-1-yl)oxyimino-2-(2-formamidothiazol-4-yl)acetamido]-3-(1H-tetrazol-5-yl)thiomethyl-3-cephem-4-carboxylic acid (syn isomer).
I.R. (Nujol): 3400–3100, 1770, 1660, 1540 cm$^{-1}$

(29) 7-[2-(2-Cyclopenten-1-yl)oxyimino-2-(2-aminothiazol-4-yl)acetamido]-3-[1-(2-hydroxyethyl)-1H-tetrazol-5-yl]thiomethyl-3-cephem-4-carboxylic acid (syn isomer). mp. 162° to 168° C. (dec.).
I.R. (Nujol): 3400–3100, 1770, 1720, 1650, 1540 cm$^{-1}$

(30) 7-[2-(2-Cyclopenten-1-yl)oxyimino-2-(2-formamidothiazol-4-yl)acetamido-3-[1-(2-hydroxyethyl)-1H-tetrazol-5-yl]thiomethyl-3-cephem-4-carboxylic acid (syn isomer).
I.R. (Nujol): 3400–3100, 1780, 1670, 1540 cm$^{-1}$

(31) 7-[2-(2-Cyclopenten-1-yl)oxyimino-2-(2-formamidothiazol-4-yl)acetamido]-3-[1-(2-carboxyethyl)-1H-tetrazol-5-yl]thiomethyl-3-cephem-4-carboxylic acid (syn isomer).
I.R. (Nujol): 3160, 1770, 1660 cm$^{-1}$

(32) 7-[2-(2-Cyclopenten-1-yl)oxyimino-2-(2-aminothiazol-4-yl)acetamido]-3-[1-(2-carboxyethyl)-1H-tetrazol-5-yl]thiomethyl-3-cephem-4-carboxylic acid (syn isomer).
I.R. (Nujol): 3270, 1765, 1660, 1630 cm$^{-1}$

(33) 7-[2-(2-Cyclopenten-1-yl)oxyimino-2-(2-aminothiazol-4-yl)acetamido]-3-(1H-1,2,3-triazol-5-yl)thiomethyl-3-cephem-4-carboxylic acid (syn isomer). mp. 175° to 185° C. (dec.)
I.R. (Nujol): 3420, 3250, 1760, 1650, 1530 cm$^{-1}$

(34) 7-[2-(2-Cyclopenten-1-yl)oxyimino-2-(2-formamidothiazol-4-yl)acetamido]-3-[1-(3-(N-tert-butoxycarbonylamino)propyl]-1H-tetrazol-5-yl]thiomethyl-3-cephem-4-carboxylic acid (syn isomer).
I.R. (Nujol): 3180, 1780, 1680 cm$^{-1}$

(35) 7-[2-(2-Cyclopenten-1-yl)oxyimino-2-(2-aminothiazol-4-yl)acetamido]-3-[1-(3-aminopropyl)-1H-tetrazol-5-yl]thiomethyl-3-cephem-4-carboxylic acid (syn isomer).
I.R. (Nujol): 3180, 1760, 1660, 1620 cm$^{-1}$

(36) 7-[2-(2-Cyclopenten-1-yl)oxyimino-2-(2-formamido-thiazol-4-yl)acetamido]-3-(tetrazolo[1,5-b]pyridazin-6-yl)thiomethyl-3-cephem-4-carboxylic acid (syn isomer)
I.R. (Nujol): 3180, 1780, 1670 cm$^{-1}$

(37) 7-[2-(2-Cyclopenten-1-yl)oxyimino-2-(2-aminothiazol-4-yl)acetamido]-3-(tetrazolo[1,5-b]pyridazin-6-yl)thiomethyl-3-cephem-4-crboxylic acid (syn isomer). mp. 178° to 180° C. (dec.).
I.R. (Nujol): 3280, 3180, 1770, 1650, 1620 cm$^{-1}$

(38) 7-[2-(2-Cyclohexen-1-yl)oxyimino-2-(2-formamidothiazol-4-yl)acetamido]-3-[1-(2-carboxyethyl)-

1H-tetrazol-5-yl]thiomethyl-3-cephem-4-carboxylic acid (syn isomer).

I.R. (Nujol): 3180, 1770, 1660 cm$^{-1}$

(39) 7-[2-(2-Cyclohexen-1-yl)oxyimino-2-(2-aminothiazol-4-yl)acetamido]-3-[1-(2-carboxyethyl)-1H-tetrazol-5-yl]thiomethyl-3-cephem-4-carboxylic acid (syn isomer).

I.R. (Nujol): 3300, 3200, 1770, 1660, 1630 cm$^{-1}$

(40) N-[7-[2-(2-Cyclopenten-1-yl)oxyimino-2-(2-aminothiazol-4-yl)acetamido]-3-cephem-3-ylmethyl]-3'-carbamoylpyridinium-4-carboxylate (syn isomer).

I.R. (Nujol): 3400–3200, 1780, 1680, 1615, 1530 cm$^-$

N.M.R. (D$_2$O+DCL, δ): 1.5–2.72 (4H, m), 3.53, 4.00 (2H,q, J=18 Hz), 5.33–6.50 (5H, m), 5.43 (1H, d, J=5 Hz), 6.00 (1H, d,J=5 Hz), 7.20 (1H, s), 8.40 (1H, dd, J=6 and 6 Hz), 9.00–9.47 (2H,m), 9.53 (1H, s)

EXAMPLE 24

To a solution of benzhydryl 7-[2-(2-cyclopenten-1-yl)oxyimino-2-(2-aminothiazol-4-yl)acetamido]-3-(2-tert-butoxycarboxamidoethyl)thiomethyl-3-cephem-4-carboxylate (syn isomer) (2.7 g) in methylene chloride (20 ml) were added trifluoroacetic acid (7.8 g) and anisole (2.2 g) under ice-cooling. The mixture was stirred for 50 minutes at room temperature. The reaction mixture was evaporated and to the residue was added a mixture of chilled water and ethyl acetate. The mixture was adjusted to pH 7.5 with 20% aqueous solution of sodium bicarbonate. The aqueous layer was separated, washed with ethyl acetate and thereto was added ethyl acetate. The mixture was adjusted to pH 2 with 10% hydrochloric acid. The aqueous layer was separated, adjusted to pH 6 with a saturated aqueous solution of sodium bicarbonate and evaporated. The residue was adjusted to pH 3.8 with 10% hydrochloric acid and subjected to column chromatography (Non-ion adsorption resin, Diaion HP20 prepared by Mitsubishi Chemical Industries) using 30% isopropyl alcohol as an eluent. Fractions containing the object compounds were collected and evaporated. The residue was lyophilized to give 7-[2-(2-cyclopenten-1-yl)oxyimino-2-(2-aminothiazol-4-yl)acetamido]-3-(2-aminoethyl)thiomethyl-3-cephem-4-carboxylic acid (syn isomer)(1.0 g).

I.R. (Nujol): 3350–3100, 1760, 1660, 1610, 1515 cm$^{-1}$

N.M.R. (DMSO-d$_6$, δ) 1.60–3.24 (6H, m), 3.24–3.90 (6H, m), 5.08 (1H, d, J=5 Hz), 5.26 (1H, m), 5.64 (1H, dd, J=5 and 8 Hz), 5.76–6.2 (2H, m), 6.72 (1H, s), 9.44 (1H, d, J=8 Hz)

EXAMPLE 25

The following compounds were prepared according to a similar manner to that of Example 24.

(1) 7-[2-(2-Cyclopenten-1-yl)oxyimino-2-(2-aminothiazol-4-yl)acetamido]-3-cephem-4-carboxylic acid (syn isomer). mp. 201° to 213° C. (dec.).

I.R. (Nujol): 3400–3100, 1770, 1650, 1620, 1540 cm$^{-1}$ (2) 7-[2-(2-Cyclopenten-1-yl)oxyimino-2-(2-aminothiazol-4-yl)acetamido]-2-methyl-3-cephem-4-carboxylic acid (syn isomer).

I.R. (Nujol): 3300, 1770, 1660, 1630 cm$^{-1}$ (3) 7-[2-(2-Cyclopenten-1-yl)oxyimino-2-(2-aminothiazol-4-yl)acetamido]cephalosporanic acid (syn isomer). mp. 141° to 150° C. (dec.).

I.R. (Nujol): 3400–3100, 1770, 1730, 1650, 1530 cm$^{-1}$ (4) 7-[2-(2-Cyclopenten-1-yl)oxyimino-2-(2-aminothiazol-4-yl)acetamido]-3-carbamoyloxymethyl-3-cephem-4-carboxylic acid (syn isomer). mp. 182° to 195° C. (dec.).

I.R. (Nujol): 3250, 1760, 1700, 1650, 1540 cm$^{-1}$ (5) 7-[2-(2-Cyclopenten-1-yl)oxyimino-2-(2-aminothiazol-4-yl)acetamido]-3-(1,3,4-thiadiazol-2-yl)thiomethyl-3-cephem-4-carboxylic acid (syn isomer). mp. 152° to 157° C. (dec.).

I.R. (Nujol): 3340, 1775, 1655 cm$^{-1}$ (6) 7-[2-(2-Cyclopenten-1-yl)oxyimino-2-(2-aminothiazol-4-yl)acetamido]-3-(5-methyl-1,3,4-thiadiazol-2-yl)thiomethyl-3-cephem-4-carboxylic acid (syn isomer). mp. 148° to 152° C.

I.R. (Nujol): 3260, 1770, 1650 cm$^{-1}$ (7) 7-[2-(2-Cyclopenten-1-yl)oxyimino-2-(2-aminothiazol-4-yl)acetamido]-3-(1-methyl-1H-tetrazol-5-yl)thiomethyl-3-cephem-4-carboxylic acid (syn isomer). mp. 147° to 150° C.

I.R. (Nujol): 3300, 1770, 1660 cm$^{-1}$ (8) 7-[2-(2-Cyclopenten-1-yl)oxyimino-2-(2-aminothiazol-4-yl)acetamido]-3-(1-allyl-1H-tetrazol-5-yl)thiomethyl-3-cephem-4-carboxylic acid (syn isomer). mp. 145° to 153° C. (dec.).

I.R. (Nujol): 3400–3100, 1770, 1670, 1620, 1520 cm$^{-1}$ (9) 7-[2-(2-Cyclopenten-1-yl)oxyimino-2-(2-aminothiazol-4-yl)acetamido]-3-(1-carboxymethyl-1H-tetrazol-5-yl)thiomethyl-3-cephem-4-carboxylic acid (syn isomer). mp. 164° to 170° C. (dec.).

I.R. (Nujol): 3280, 1765, 1655 cm$^{-1}$

(10) 7-[2-(2-Cyclopenten-1-yl)oxyimino-2-(2-aminothiazol-4-yl)acetamido]-3-(4-carboxypyridin-2-yl)thiomethyl-3-cephem-4-carboxylic acid (syn isomer). mp. 174° to 205° C. (dec.).

I.R. (Nujol): 1760, 1670, 1620, 1450, 1370, 1360 cm$^{-1}$

(11) 7-[2-(2-Cyclopenten-1-yl)oxyimino-2-(2-aminothiazol-4-yl)acetamido]-3-(1H-tetrazol-5-yl)thiomethyl-3-cephem-4-carboxylic acid (syn isomer). mp. 165° to 172° C. (dec.).

I.R. (Nujol): 3300, 1770, 1660, 1630 cm$^{-1}$

(12) 7-[2-(2-Cyclopenten-1-yl)oxyimino-2-(2-aminothiazol-4-yl)acetamido]-3-(5-aminomethyl-1,3,4-thiadiazol-2-yl)thiomethyl-3-cephem-4-carboxylic acid (syn isomer). mp. 145° to 170° C. (dec.).

I.R. (Nujol): 3150, 1760, 1650, 1610, 1520 cm$^{-1}$

(13) 7-[2-(2-Cyclohexen-1-yl)oxyimino-2-(2-aminothiazol-4-yl)acetamido]-3-cephem-4-carboxylic acid (syn isomer). mp. 220° to 241° C. (dec.).

I.R. (Nujol): 3400–3100, 1770, 1650, 1630, 1530 cm$^{-1}$

(14) 7-[2-(2-Cyclohexen-1-yl)oxyimino-2-(2-aminothiazol-4-yl)acetamido]-2-methyl-3-cephem-4-carboxylic acid (syn isomer). mp. 159° to 166° C. (dec.).

I.R. (Nujol): 3400–3100, 1770, 1660, 1630, 1520 cm$^{-1}$

(15) 7-[2-(2-Cyclohexen-1-yl)oxyimino-2-(2-aminothiazol-4-yl)acetamido]-3-(1,3,4-thiadiazol-2-yl)thiomethyl-3-cephem-4-carboxylic acid (syn isomer).

I.R. (Nujol): 3400–3100, 1770, 1660, 1620, 1530 cm$^{-1}$

(16) 7-[2-(2-Cyclohexen-1-yl)oxyimino-2-(2-aminothiazol-4-yl)acetamido]-3-(1-methyl-1H-tetrazol-5-yl)thiomethyl-3-cephem-4-carboxylic acid (syn isomer). mp. 156° to 160° C. (dec.).

I.R. (Nujol): 3400–3100, 1770, 1660, 1620, 1520 cm$^{-1}$

(17) 7-[2-(2-Cyclohexen-1-yl)oxyimino-2-(2-aminothiazol-4-yl)acetamido]-3-(1-allyl-1H-tetrazol-5-yl)thiomethyl-3-cephem-4-carboxylic acid (syn isomer). mp. 148° to 157° C. (dec.).

I.R. (Nujol): 3400–3100, 1770, 1670, 1620, 1520 cm$^{-1}$

(18) 7-[2-(2-Cyclohexen-1-yl)oxyimino-2-(2-aminothiazol-4-yl)acetamido]-3-(1-carboxymethyl-1H-tetrazol-5-yl)thiomethyl-3-cephem-4-carboxylic acid (syn isomer). mp. 166° to 182° C. (dec.).

I.R. (Nujol): 3400–3100, 1770, 1660, 1620, 1530 cm$^{-1}$

(19) 7-[2-(2-Cyclohexen-1-yl)oxyimino-2-(2-aminothiazol-4-yl)acetamido]-3-(1H-tetrazol-5-yl)thiomethyl-3-cephem-4-carboxylic acid (syn isomer).

(20) 7-[2-(2-Cyclopenten-1-yl)oxyimino-2-(2-formamidothiazol-4-yl)acetamido]-3-cephem-4-carboxylic acid (syn isomer). mp. 145° to 170° C. (dec.).

I.R. (Nujol): 3400–3100, 1780, 1680, 1650, 1540 cm$^{-1}$

(21) 7-[2-(2-Cyclopenten-1-yl)oxyimino-2-(2-formamidothiazol-4-yl)acetamido]-2-methyl-3-cephem-4-carboxylic acid (syn isomer).

I.R. (Nujol): 3260, 1780, 1680, 1660 cm$^{-1}$

(22) 7-[2-(2-Cyclopenten-1-yl)oxyimino-2-{2-(2,2,2-trifluoroacetamido)thiazol-4-yl}acetamido]cephalosporanic acid (syn isomer).

I.R. (Nujol): 3400–3100, 1780, 1730, 1660, 1580, 1510 cm$^{-1}$

(23) 7-[2-(2-Cyclopenten-1-yl)oxyimino-2-(2-formamidothiazol-4-yl)acetamido]-3-carbamoyloxymethyl-3-cephem-4-carboxylic acid (syn isomer).

I.R. (Nujol): 3450, 3260, 1770, 1700, 1660, 1640, 1610, 1550 cm$^{-1}$

(24) 7-[2-(2-Cyclopenten-1-yl)oxyimino-2-(2-formamidothiazol-4-yl)acetamido]-3-(1,3,4-thiadiazol-2-yl)thiomethyl-3-cephem-4-carboxylic acid (syn isomer).

I.R. (Nujol): 3150, 1770, 1670 cm$^{-1}$

(25) 7-[2-(2-Cyclopenten-1-yl)oxyimino-2-(2-formamidothiazol-4-yl)acetamido]-3-(5-methyl-1,3,4-thiadiazol-2-yl)thiomethyl-3-cephem-4-carboxylic acid (syn isomer).

I.R. (Nujol): 3240, 1765, 1660 cm$^{-1}$

(26) 7-[2-(2-Cyclopenten-1-yl)oxyimino-2-(2-formamidothiazol-4-yl)acetamido]-3-(1-methyl-1H-tetrazol-5-yl)thiomethyl-3-cephem-4-carboxylic acid (syn isomer).

I.R. (Nujol): 3240, 1760, 1670 cm$^{-1}$

(27) 7-[2-(2-Cyclopenten-1-yl)oxyimino-2-(2-formamidothiazol-4-yl)acetamido]-3-(1-allyl-1H-tetrazol-5-yl)thiomethyl-3-cephem-4-carboxylic acid (syn isomer). mp. 120° to 139° C. (dec.).

I.R. (Nujol): 3400–3100, 1770, 1670, 1540 cm$^{-1}$

(28) 7-[2-(2-Cyclopenten-1-yl)oxyimino-2-(2-formamidothiazol-4-yl)acetamido]-3-(1-carboxymethyl-1H-tetrazol-5-yl)thiomethyl-3-cephem-4-carboxylic acid (syn isomer).

I.R. (Nujol): 3150, 1770, 1660 cm$^{-1}$

(29) 7-[2-(2-Cyclopenten-1-yl)oxyimino-2-(2-formamidothiazol-4-yl)acetamido]-3-(4-carboxypyridin-2-yl)thiomethyl-3-cephem-4-carboxylic acid (syn isomer).

I.R. (Nujol): 1770, 1690–1650, 1540 cm$^{-1}$

(30) 7-[2-(2-Cyclopenten-1-yl)oxyimino-2-(2-formamidothiazol-4-yl)acetamido]-3-(1H-tetrazol-5-yl)thiomethyl-3-cephem-4-carboxylic acid (syn isomer).

I.R. (Nujol): 1770, 1660 cm$^{-1}$

(31) 7-[2-(2-Cyclohexen-1-yl)oxyimino-2-(2-formamidothiazol-4-yl)acetamido]-3-cephem-4-carboxylic acid (syn isomer). mp. 155° to 185° C. (dec.).

I.R. (Nujol): 3400–3100, 1780, 1690, 1660, 1630, 1540 cm$^{-1}$

(32) 7-[2-(2-Cyclohexen-1-yl)oxyimino-2-(2-formamidothiazol-4-yl)acetamido]-2-methyl-3-cephem-4-carboxylic acid (syn isomer).

I.R. (Nujol): 3275, 3175, 1780, 1690, 1660, 1620, 1570, 1530 cm$^{-1}$

(33) 7-[2-(2-Cyclohexen-1-yl)oxyimino-2-(2-formamidothiazol-4-yl)acetamido]-3-(1,3,4-thiadiazol-2-yl)thiomethyl-3-cephem-4-carboxylic acid (syn isomer).

I.R. (Nujol): 3300–3100, 1780, 1670, 1540 cm$^{-1}$

(34) 7-[2-(2-Cyclohexen-1-yl)oxyimino-2-(2-formamidothiazol-4-yl)acetamido]-3-(1-methyl-1H-tetrazol-5-yl)thiomethyl-3-cephem-4-carboxylic acid (syn isomer).

I.R. (Nujol): 3400–3100, 1780, 1660, 1550 cm$^{-1}$

(35) 7-[2-(2-Cyclohexen-1-yl)oxyimino-2-(2-formamidothiazol-4-yl)acetamido]-3-(1-allyl-1H-tetrazol-5-yl)thiomethyl-3-cephem-4-carboxylic acid (syn isomer).

I.R. (Nujol): 3400–3100, 1770, 1670, 1540 cm$^{-1}$

(36) 7-[2-(2-Cyclohexen-1-yl)oxyimino-2-(2-formamidothiazol-4-yl)acetamido]-3-(1-carboxymethyl-1H-tetrazol-5-yl)thiomethyl-3-cephem-4-carboxylic acid (syn isomer)

I.R. (Nujol): 3400–3100, 1770, 1670, 1540 cm$^{-1}$

(37) 7-[2-(2-Cyclohexen-1-yl)oxyimino-2-(2-formamidothiazol-4-yl)acetamido]-3-(1H-tetrazol-5-yl)thiomethyl-3-cephem-4-carboxylic acid (syn isomer).

I.R. (Nujol): 3400–3100, 1770, 1660, 1540 cm$^{-1}$

(38) 7-[2-(2-Cyclopenten-1-yl)oxyimino-2-(2-aminothiazol-4-yl]acetamido]-3-{1-(2-hydroxyethyl)-1H-tetrazol-5-yl}thiomethyl-3-cephem-4-carboxylic acid (syn isomer). mp. 162° to 168° C. (dec.).

I.R. (Nujol): 3400–3100, 1770, 1720, 1650, 1540 cm$^{-1}$

(39) 7-[2-(2-Cyclopenten-1-yl)oxyimino-2-(2-formamidothiazol-4-yl)acetamido]-3-{1-(2-hydroxyethyl)-1H-tetrazol-5-yl}thiomethyl-3-cephem-4-carboxylic acid (syn isomer).

I.R. (Nujol): 3400–3100, 1780, 1670, 1540 cm$^{-1}$

(40) 7-[2-(2-Cyclohexen-1-yl)oxyimino-2-(2-aminothiazol-4-yl)acetamido]cephalosporanic acid (syn isomer).

I.R. (Nujol): 3400–3100, 1770, 1740, 1660, 1630, 1520 cm$^{-1}$

(41) 7-[2-(2-Cyclopenten-1-yl)oxyimino-2-(2-formamidothiazol-4-yl)acetamido]-3-[1-(2-carboxyethyl)-1H-tetrazol-5-yl]thiomethyl-3-cephem-4-carboxylic acid (syn isomer).

I.R. (Nujol): 3160, 1770, 1660 cm$^{-1}$

(42) 7-[2-(2-Cyclopenten-1-yl)oxyimino-2-(2-aminothiazol-4-yl)acetamido]-3-[1-(2-carboxyethyl)-1H-tetrazol-5-yl]thiomethyl-3-cephem-4-carboxylic acid (syn isomer).

I.R. (Nujol): 3270, 1765, 1660, 1630 cm$^{-1}$

(43) 7-[2-(2-Cyclopenten-1-yl)oxyimino-2-{2-(2,2,2-trifluoroacetamido)thiazol-4-yl}acetamido]-3-(1H-1,2,3-triazol-5-yl)thiomethyl-3-cephem-4-carboxylic acid (syn isomer).

I.R. (Nujol): 3250, 1780, 1730, 1660, 1590, 1540 cm$^{-1}$

(44) 7-[2-(2-Cyclopenten-1-yl)oxyimino-2-(2-aminothiazol-4-yl)acetamido]-3-(1H-1,2,3-triazol-5-yl)thiomethyl-3-cephem-4-carboxylic acid (syn isomer). mp. 175° to 185° C. (dec.).

I.R. (Nujol): 3420, 3250, 1760, 1650, 1530 cm$^{-1}$

(45) 7-[2-(2-Cyclopenten-1-yl)oxyimino-2-(2-formamidothiazol-4-yl)acetamido]-3-[1-(3-(N-tertbutoxycarbonylamino)propyl]-1H-tetrazol-5-yl]thiomethyl-3-cephem-4-carboxylic acid (syn isomer).

I.R. (Nujol): 3180, 1780, 1680 cm$^{-1}$

(46) 7-[2-(2-Cyclopenten-1-yl)oxyimino-2-(2-aminothiazol-4-yl)acetamido]-3-[1-(3-aminopropyl)-1H-tetrazol-5-yl]thiomethyl-3-cephem-4-carboxylic acid (syn isomer).

I.R. (Nujol): 3180, 1760, 1660, 1620 cm$^{-1}$

7-[2-(2-Cyclopenten-1-yl)oxyimino-2-(2-formamidothiazol-4-yl)acetamido]-3-(tetrazolo[1,5-b]pyridazin-6-yl)thiomethyl-3-cephem-4-carboxylic acid (syn isomer)

I.R. (Nujol): 3180, 1780, 1670 cm$^{-1}$

(48) 7-[2-(2-Cyclopenten-1-yl)oxyimino-2-(2-aminothiazol-4-yl)acetamido]-3-(tetrazolo[1,5-b]pyridazin-6-yl)thiomethyl-3-cephem-4-carboxylic acid (syn isomer). mp. 178° to 180° C. (dec.).

I.R. (Nujol): 3280, 3180, 1770, 1650, 1620 cm$^{-1}$

(49) 7-[2-(2-Cyclohexen-1-yl)oxyimino-2-(2-formamidothiazol-4-yl)acetamido]-3-carbamoyloxymethyl-3-cepehm-4-carboxylic acid (syn isomer).

I.R. (Nujol): 3260, 1780, 1680 (broad), 1540 cm$^{-1}$

(50) 7-[2-(2-Cyclohexen-1-yl)oxyimino-2-(2-aminothiazol-4-yl)acetamido]-3-carbamoyloxymethyl-3-cephem-4-carboxylic acid (syn isomer). mp. 230° to 235° C. (dec.).

I.R. (Nujol): 3440, 3330, 3270, 1750, 1690, 1630, 1530 cm$^{-1}$

(51) 7-[2-(2-Cyclohexen-1-yl)oxyimino-2-(2-formamidothiazol-4-yl)acetamido]-3-[1-(2-carboxyethyl)-1H-tetrazol-5-yl]thiomethyl-3-cephem-4-carboxylic acid (syn isomer).

I.R. (Nujol): 3180, 1770, 1660 cm$^{-1}$

(52) 7-[2-(2-Cyclohexen-B 1-yl)oxyimino-2-(2-aminothiazol-4-yl)acetamido]-3-[1-(2-carboxyethyl)-1H-tetrazol-5-yl]thiomethyl-3-cephem-4-carboxylic acid (syn isomer).

I.R. (Nujol): 3300, 3200, 1770, 1660, 1630 cm$^{-1}$

EXAMPLE 26

To a solution of 7-[2-(2-cyclopenten-1-yl)oxyimino-2-(2-formamidothiazol-4-yl)acetamido]-3-[1-[3-(N-tert-butoxycarbonylamino)propyl]-1H-tetrazol-5-yl]thiomethyl-3-cephem-4-carboxylic acid (syn isomer) (1.75 g) in methanol (13 ml) was added conc.hydrochloric acid (1.0 g) with stirring and the mixture was stirred for 3 hours at room temperature. After the evaporation of the resulting mixture, to the residue was added methanol (20 ml) to give a homogeneous solution and then the solution was evaporated. Solution and evaporation were repeated three times and to the resulting reaction mixture were added ethyl acetate and water. After the mixture was adjusted to pH 7.5 with sodium bicarbonate, the aqueous layer was separated, washed with ethyl acetate and the remaining ethyl acetate was distilled off. The resulting aqueous layer was adjusted to pH 3.8 with 1 N hydrochloric acid and then filtered. The precipitates thus collected were washed with water and dried over phosphorus pentoxide under reduced pressure to give 7-[2-(2-cyclopenten-1-yl)oxyimino-2-(2-aminothiazol-4-yl)acetamido]-3-[1-(3-aminopropyl)-1H-tetrazol-5-yl]thiomethyl-3-cephem-4-carboxylic acid (syn isomer)(0.31 g).

I.R. (Nujol): 3180, 1760, 1660, 1620 cm$^{-1}$

N.M.R. (DMSO-d$_6$,δ): 1.68–2.60 (4H, m), 2.96 (2H, m), 3.51 (2H, m), 4.06–4.67 (4H, m), 5.01 (1H, d, J=5.0 Hz), 5.26 (1H, m), 5.47–6.28 (3H, m), 6.70 (1H, s), 9.45 (1H, d, J=8.0 Hz)

The filtrate was subjected to column chromatography (non-ion adsorption resin, Diaion HP20 prepared by Mitsubishi Chemical Industries) (60 ml), washed with water and eluted with 15 to 20% isopropyl alcohol. The fractions containing the object compound were combined, concentrated and then lyophilized to give the same compound (0.31 g).

EXAMPLE 27

The following compounds were prepared according to a similar manner to those of Example 26.

(1) 7-[2-(2-Cyclopenten-1-yl)oxyimino-2-(2-aminothiazol-4-yl)acetamido]-3-(2-aminoethyl)thiomethyl-3-cephem-4-carboxylic acid (syn isomer).

I.R. (Nujol): 3350-3100, 1760, 1660, 1610, 1515 cm$^{-}$ (2) 7-[2-(2-Cyclopenten-1-yl)oxyimino-2-(2-aminothiazol-4-yl)acetmido]-3-(5-aminomethyl-1,3,4-thiadiazol-2-yl)thiomethyl-3-cephem-4-carboxylic acid (syn isomer). mp 145° to 170° C. (dec.).

I.R. (Nujol): 3150, 1760, 1650, 1610, 1520 cm$^{-1}$ (3) 7-[2-(2-Cyclopenten-1-yl)oxyimino-2-(2-formamidothiazol-4-yl)acetamido]-3-carbamoyloxymethyl-3-cephem-4-carboxylic acid (syn isomer).

I.R. (Nujol): 3450, 3260, 1770, 1700, 1660, 1640, 1610, 1550 cm$^{-1}$ (4) 7-[2-(2-Cyclopenten-1-yl)oxyimino-2-(2-aminothiazol-4-yl)acetamido]-3-carbamoyloxymethyl-3-cephem-4-carboxylic acid (syn isomer). mp. 182° to 195° C. (dec.).

I.R. (Nujol): 3250, 1760, 1700, 1650, 1540 cm$^{-1}$ (5) 7-[2-(2-Cyclohexen-1-yl)oxyimino-2-(2-formamidothiazol-4-yl)acetamido]-3-carbamoyloxymethyl-3-cephem-4-carboxylic acid (syn isomer).

I.R. (Nujol): 3260, 1780, 1680 (broad), 1540 cm$^{-1}$ (6) 7-[2-(2-Cyclohexen-1-yl)oxyimino-2-(2-aminothiazol-4-yl)acetamido]-3-carbamoyloxymethyl-3-cephem-4-carboxylic acid (syn isomer).

mp. 230° to 235° C. (dec.).

I.R. (Nujol): 3440, 3330, 3270, 1750, 1690, 1630, 1530 cm$^{-1}$

What we claim is:

1. A cephem compound of the formula:

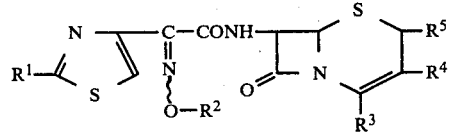

wherein $R^1$ is amino or a protected amino group;

$R^2$ is cyclopentenyl or cyclohexenyl;

$R^3$ is carboxy or a protected carboxy group;

$R^4$ is a group of the formula:

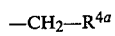

wherein $R^{4a}$ is lower alkanoyloxy or thiadiazolylthio; and $R^5$ is hydrogen or lower alkyl; and pharmaceutically acceptable salts thereof.

2. The compound of claim 1 wherein:

$R^1$ is amino or acylamino;

$R^3$ is carboxy or esterified carboxy; and $R^4$ is a group of the formula:

wherein $R^{4a}$ is lower alkanoyloxy or thiadiazolylthio.

3. The compound of claim 2, which is syn isomer.

4. The compound of claim 3, wherein $R^1$ is amino;

$R^2$ is cyclopentenyl or cyclohexenyl;

$R^3$ is carboxy;

$R^{4a}$ is lower alkanoyloxy; and $R^5$ is hydrogen.

5. The compound of claim 4, which is 7-[2-(2-cyclopenten-1-yl)oxyimino-2-(2-aminothiazol-4-yl)acetamido]cephalosporanic acid (syn isomer).

6. The compound of claim 4 which is 7-[2-(2-cyclohexen-1-yl)oxyimino-2-(2-aminothiazol-4-yl)acetamido]cephalosporanic acid (syn isomer).

7. The compound of claim 3, wherein $R^1$ is amino;

$R^3$ is carboxy;

$R^{4a}$ is thiadiazolylthio, and $R^5$ is hydrogen.

8. The compound of claim 7, which is 7-[2-(2-cyclopenten-1-yl)oxyimino-2-(2-aminothiazol-4- yl)acetamido]-3-(1,3,4-thiadiazol-2-yl)thiomethyl-3-cephem-4-carboxylic acid (syn isomer).

9. The compound of claim 7, which is 7-[2-cyclohexen-1-yl)oxyimino-2-[2-aminothiazol-4-yl)acetamido]-3-(1,3,4-thiadiazol-2-yl)thiomethyl-3-cephem-4-carboxylic acid (syn isomer).

10. The compound of claim 3, wherein $R^1$ is lower alkanoylamino or halogen substituted lower alkanoylamino; and
$R^3$ is carboxy or ar(lower)alkoxycarbonyl.

11. A pharmaceutical composition comprising an effective amount of a compound of claim 1 or pharmaceutically acceptable salt thereof in association with a pharmaceutically acceptable, substantially non-toxic carrier or excipient.

* * * * *